United States Patent
Mochly-Rosen et al.

(10) Patent No.: US 7,803,775 B2
(45) Date of Patent: *Sep. 28, 2010

(54) PROTEIN KINASE C PEPTIDES FOR USE IN WITHDRAWAL

(75) Inventors: Daria Mochly-Rosen, Menlo Park, CA (US); Joan J. Kendig, Campbell, CA (US); Sarah M. Sweitzer, Vallejo, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 11/805,436

(22) Filed: May 22, 2007

(65) Prior Publication Data

US 2008/0262199 A1    Oct. 23, 2008

Related U.S. Application Data

(63) Continuation of application No. 11/030,794, filed on Jan. 7, 2005, now Pat. No. 7,235,526, which is a continuation of application No. 10/428,280, filed on May 1, 2003, now Pat. No. 6,933,275.

(60) Provisional application No. 60/377,331, filed on May 1, 2002.

(51) Int. Cl.
*A61K 38/08* (2006.01)
*C07K 7/06* (2006.01)

(52) U.S. Cl. .............................. 514/17; 514/2; 530/329

(58) Field of Classification Search ........................ None
See application file for complete search history.

(56) References Cited

U.S. PATENT DOCUMENTS

| 5,783,405 | A  | 7/1998  | Mochly-Rosen et al. |
| 5,846,974 | A  | 12/1998 | Kallman et al. |
| 6,165,977 | A  | 12/2000 | Mochly-Rosen |
| 6,180,620 | B1 | 1/2001  | Salvemini |
| 6,376,467 | B1 | 4/2002  | Messing et al. |
| 6,395,306 | B1 | 5/2002  | Cui et al. |

(Continued)

FOREIGN PATENT DOCUMENTS

WO    WO 00/01415 A2    1/2000

(Continued)

OTHER PUBLICATIONS

Aley et al., *The Journal of Neuroscience*, 20(12):4680-4685 (2000).

(Continued)

*Primary Examiner*—Jeffrey E Russel
(74) *Attorney, Agent, or Firm*—Judy M. Mohr; Susan L. Harlocker; King & Spalding LLP

(57) ABSTRACT

A method for managing withdrawal from an addictive substance is described. The method involves administering one or more peptides having specific activity for the $\epsilon$ and/or $\gamma$ isozyme of protein kinase C (PKC). The peptide(s) can be administered prior to, concurrent with, or subsequent to administration of the addictive substance. Also described is a kit having at least one container containing a peptide having isozyme-specific activity for $\epsilon$PKC or $\gamma$PKC and instructions for use.

6 Claims, 16 Drawing Sheets

U.S. PATENT DOCUMENTS

| | | | |
|---|---|---|---|
| 6,686,334 | B2 | 2/2004 | Messing et al. |
| 6,933,275 | B2 | 8/2005 | Mochly-Rosen et al. |
| 7,235,526 | B2 | 6/2007 | Mochly-Rosen et al. |
| 7,459,424 | B2 * | 12/2008 | Mochly-Rosen et al. ....... 514/2 |
| 2002/0124272 | A1 | 9/2002 | Messing et al. |
| 2003/0166037 | A1 | 9/2003 | Fourie et al. |
| 2003/0223981 | A1 | 12/2003 | Mochly-Rosen et al. |

FOREIGN PATENT DOCUMENTS

| | | |
|---|---|---|
| WO | WO 00/01805 | 1/2000 |
| WO | WO 03/089457 A2 | 10/2003 |

OTHER PUBLICATIONS

Dina et al., *The Journal of Neuroscience*, 20(22):8614-8619 (2000).
Johnson et al., *The Journal of Biol. Chem.*, 271(40):24962-24966 (1996).
Mitchell et al., *Journal of Peptide Research*, 56:318-325 (2000).
Narita et al., *The Journal of Neuroscience*, 21(11):3715-3720 (2001).
Schwarze et al., *Science*, 285:1569-1572 (1999).
Choi, D. et al., "Conditional rescue of protein kinase C epsilon regulates ethanol preference and hypnotic sensitivity in adult mice" *The Journal of Neuroscience*, 22(22):9905-9911 (2002).
Li, H.F. et al., "Protein Kinase Cγ mediates ethanol withdrawal hyperresponsiveness in spinal cord motor neurons: Electrophysiological and Immunocytochemical", Society for Neuroscience Abstract Viewer and Itinerary Planner, Neuroscience 2002 Abstract, No. 545.2 (2002).
Wong, S.M. et al., "PKCepsilon mediates naloxone-precipitated opioid withdrawal hyperresponsiveness in isolated neonatal rat spinal cord", Society for Neuroscience Abstract Viewer and Itinerary Planner, Neuroscience 2002 Abstract, No. 248.10 (2002).
Yukhananov, R.Y. et al., "Differential gene expression in PKCgamma knockout mice following chronic morphine administration", Society for Neuroscience Abstract Viewer and Itinerary Planner, Neuroscience 2001 Abstract, No. 224.6 (2001).

* cited by examiner

Control　　　　　Morphine　　　　Naloxone

Fig. 1A　　Fig. 1B　　Fig. 1C

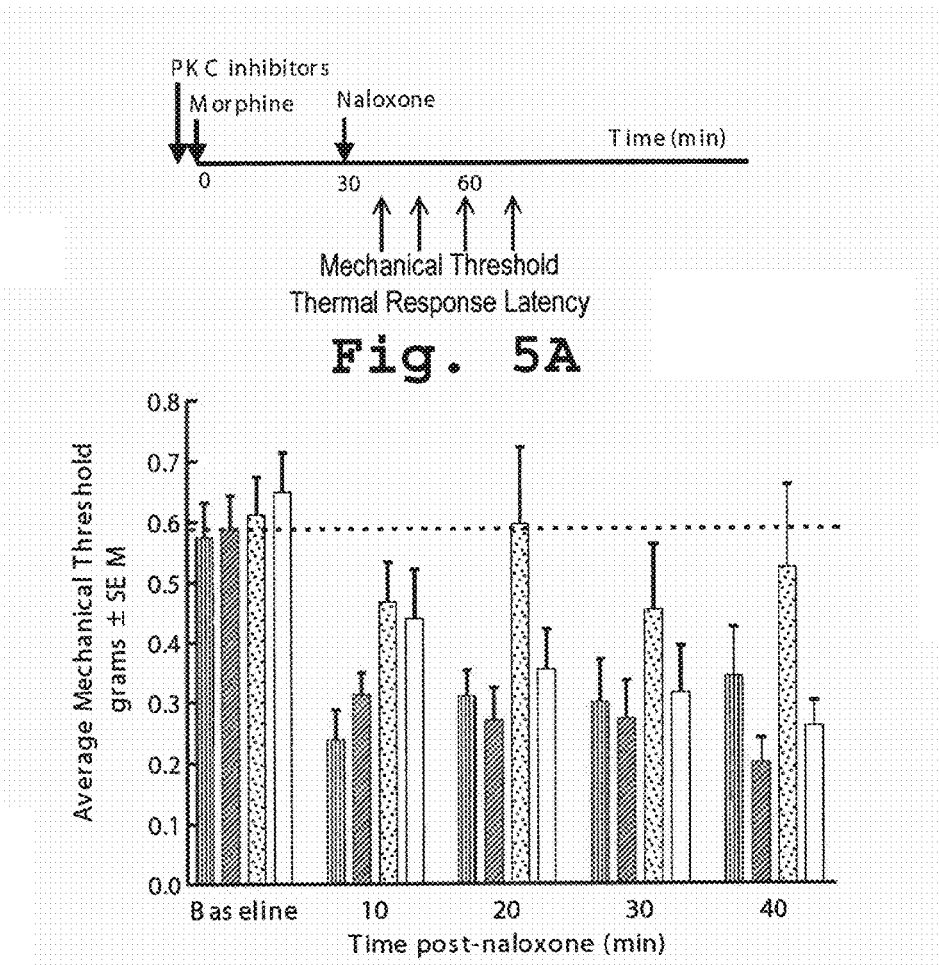
Fig. 5A
Fig. 5B
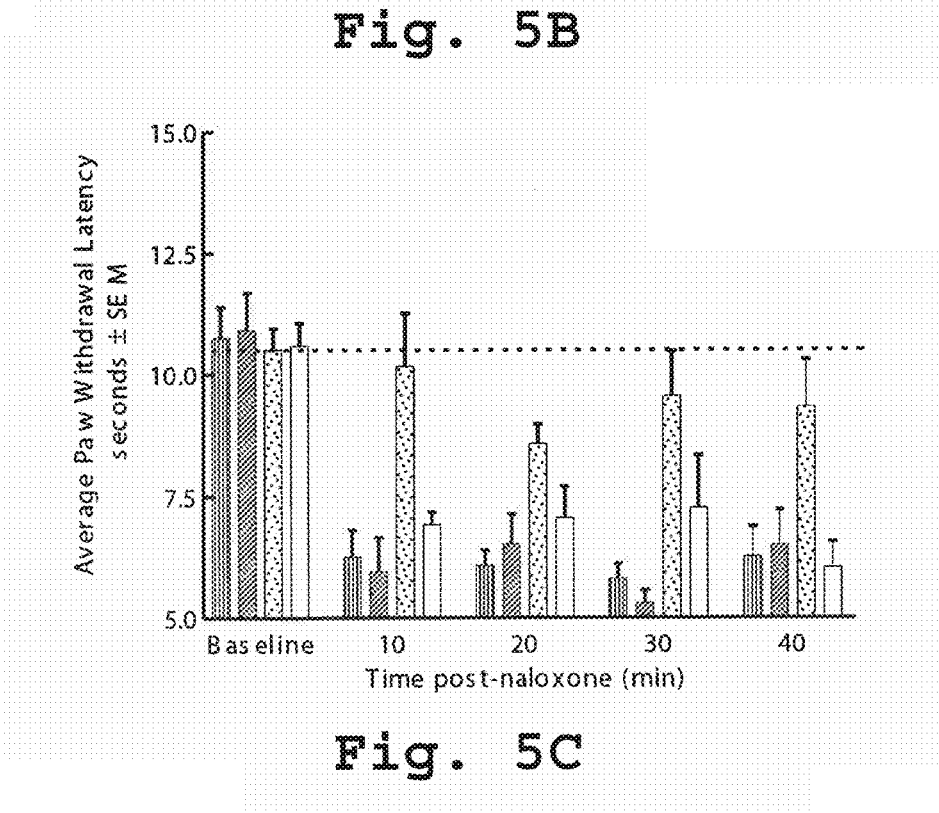
Fig. 5C

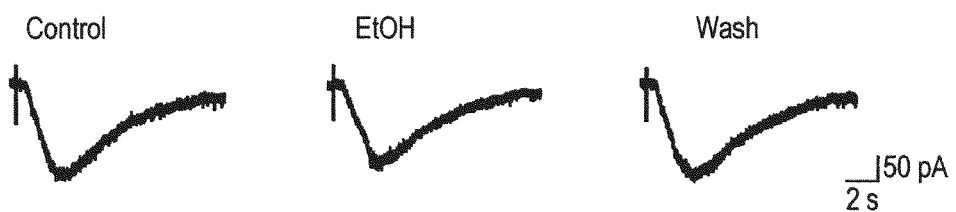
Fig. 9A    Fig. 9B    Fig. 9C
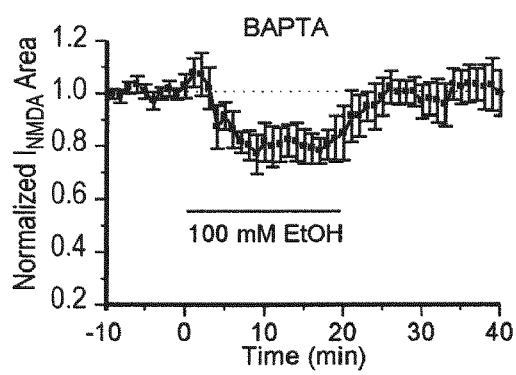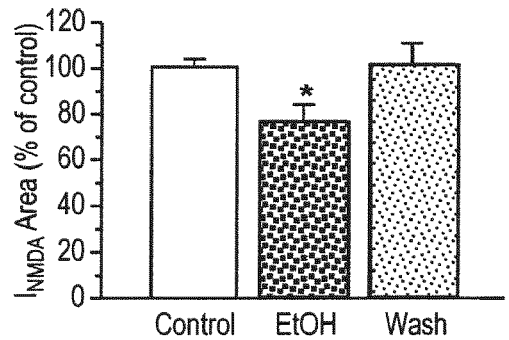
Fig. 9D    Fig. 9E

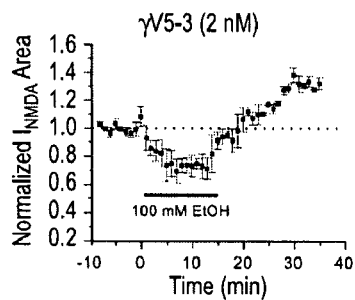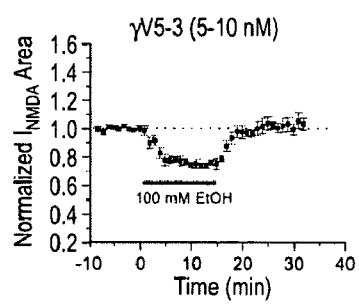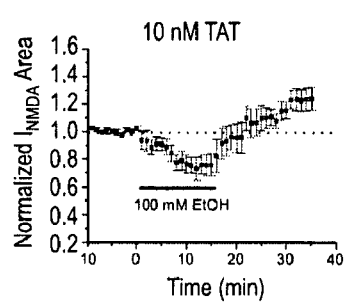
Fig. 11A  Fig. 11B  Fig. 11C
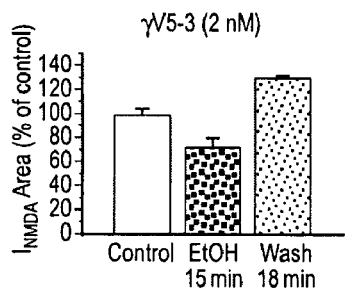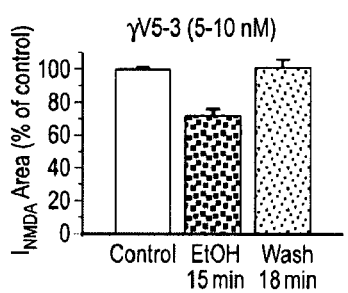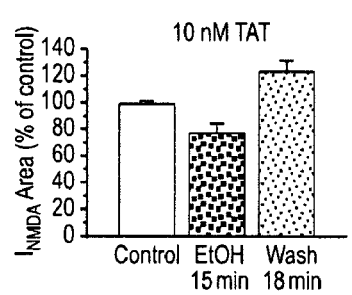
Fig. 11D  Fig. 11E  Fig. 11F

PROTEIN KINASE C PEPTIDES FOR USE IN WITHDRAWAL

CROSS-REFERENCE TO RELATED APPLICATIONS

This application is a continuation of U.S. application Ser. No. 11/030,794 filed Jan. 7, 2005 now U.S. Pat. No. 7,235,256, now pending, which is a continuation of U.S. application Ser. No. 10/428,280 filed May 1, 2003, now U.S. Pat. No. 6,933,275, which claims the benefit of U.S. Provisional Application No. 60/377,331, filed May 1, 2002, now expired, all of which are incorporated herein by reference in their entirety.

FEDERALLY-SPONSORED RESEARCH OR DEVELOPMENT

This invention was made with Government support under contract NS013108 awarded by the National Institutes of Health. The Government has certain rights in this invention.

FIELD OF THE INVENTION

The present invention relates to compositions and methods of treatment for managing the withdrawal and/or reducing the dependence of patients on habit-forming and addictive drugs, such as alcohol, narcotics, and anti-depressants.

BACKGROUND OF THE INVENTION

The repeated consumption of habit-forming drugs such as alcohol, tranquilizers, stimulants, opiates, hallucinogens and nicotine, in many instances leads to some degree of addiction. Typically, such addiction is characterized by a desire or even the need to continue use of the drug and, in some cases, by a tendency to increase its dosage. Addiction results in a psychological and physiological dependence on the effects of such drugs and eventually has a detrimental effect on the addicted individual. The prevalence of drug addiction is well accepted as imposing significant costs on society. Two main categories of motivation in addiction are the desire to experience the hedonic (e.g., rewarding) effects of the drug of abuse and the desire to avoid the anhedonia or aversive consequences of drug withdrawal.

Withdrawal from the use of habit-forming drugs is difficult and presents a serious problem, in part due to the undesirable physical and/or psychologic symptoms that accompany the abstention. Both the rewarding aspect and the aversive withdrawal aspect of addiction have been studied, the mechanism of opiate addiction in particular having been reported upon. What becomes clear from the literature is that no single brain structure is entirely responsible for addiction and addictive behaviors. Repeated use of opiates induces long lasting changes in neural pathways and neural processing in many brain regions including but not limited to the nucleus accumbens, the ventral tegmental area, basolateral amygdala, locus coeruleus, and the bed nucleus of the stria terminalis. Supraspinal brain areas are also subject to modulation by ascending input from the spinal cord. There are profound effects of opiates on spinal neurotransmission. Regardless of brain or spinal cord region examined these long lasting changes include adaptation to neurotransmitter systems which include but are not limited to glutamatergic, dopaminergic, and adrenergic signaling. These adaptations may be involved in the reinforcing hedonic aspect of addiction as well as in the aversive reinforcing aspect of addiction. Opiates act on three classes of receptors ($\mu$, $\kappa$, $\delta$) with the $\mu$-opioid receptor subtype being critical for the rewarding and aversive effects of opiates. One specific example of how opiates may mediate long lasting neuroadaptations of neural pathways and neural processing is described below.

One mechanism by which physical dependence to opiates manifests involves the noradrenergic cells of the locus ceruleus. Opiates act as agonists at inhibitory $\mu$ receptors on these cells, thereby decreasing presynaptic norepinephrine release by the cells. Over time, this results in an up-regulation of postsynaptic norepinephrine receptor expression. Concurrently, morphine down-regulates the synthesis of beta-endorphin, the normal endogenous agonist at the inhibitory $\mu$ receptors. When the opiate is withdrawn, the cell, no longer being inhibited, releases norepinephrine presynaptically. At the same time, postsynaptic supersensitivity, which results from the increase in norepinephrine receptors, leads to an amplification of the response, and an adrenergic storm ensues. This adrenergic storm manifests as a craving for more opiate, the ingestion of which re-starts and compounds the cycle.

The understanding of the central role of $\mu$-opiate receptors in the mechanism of opiate addiction has led to several abstinence-oriented strategies to treat opiate addiction. One such abstinence-oriented strategy involves the regular, typically twice weekly, administration of naltrexone, a potent, orally-effective, long-lasting $\mu$-receptor blocking agent. In another abstinence-oriented treatment, the opiate-dependent individual is maintained on buprenorphine. Because it is a partial preceptor agonist, buprenorphine has some slight reinforcing properties, and its acceptability by the opiate-dependent individual is high, as is compliance. At the same time, because it has high affinity for the $\mu$-receptor, it blocks the effects of opiates and causes the opiate-dependent individual to stop seeking them.

Alcohol is another common drug of abuse, and a major public health problem worldwide. Few drugs exist that modulate the urge for alcohol intake and the molecular causes of alcoholism remain largely uncharacterized. Disulfram (ANT-ABUSE®) was introduced in 1951 for the treatment of alcoholism via inhibition of the enzyme aldehyde dehydrogenase (involved in the metabolism of alcohol to acetic acid); the drug causes headaches, dizziness and vomiting in the presence of alcohol, negatively reinforcing the urge for alcohol intake. Furthermore, administration of naltrexone, an opiate receptor antagonist, decreases alcohol self-administration in experimental animals and relapse in human alcoholics.

There is a continuing need for compounds that can alter consumption behavior by managing the withdrawal symptoms. Like opiates, neuroadaptations in many brain regions and neurotransmitter systems underlie the rewarding aspect and the aversive aspect of alcohol addiction. Similarly, supraspinal brain areas are also subject to modulation by ascending input from the spinal cord where alcohol exerts profound effects on spinal neurotransmission.

Protein kinase C (PKC) is a family of isozymes heavily involved in signal transduction cascades. As a variety of PKC isozymes are located throughout the neuroaxis (e.g., brain, spinal cord, and primary afferent neurons) and modulate actions downstream of neurotransmitters it is likely that PKC plays a role in the actions of drugs of abuse and in the generation of withdrawal symptoms. The PKC family of isozymes are key enzymes in signal transduction involved in a variety of cellular functions, including cell growth, regulation of gene expression, and ion channel activity.

The PKC family of isozymes includes at least eleven different protein kinases that can be divided into at least three subfamilies based on their homology and sensitivity to activators. Members of the classical or cPKC subfamily, α, $β_I$, $β_{II}$ and γPKC, contain four homologous domains (C1, C2, C3 and C4) inter-spaced with isozyme-unique (variable or V) regions, and require calcium and diacylglycerol for activation. Members of the classical PKC family are found in the superficial laminae of the dorsal horn in the spinal cord as well as in numerous brain regions. Members of the novel or nPKC subfamily, δ, ε, η, and θPKC, lack the C2 homologous domain and do not require calcium for activation. PKC ε is found in primary afferent neuron terminals that innervate the spinal cord as well as in numerous brain regions. Finally, members of the atypical or αPKC subfamily, ζ and λ/ιPKC, lack both the C2 and one half of the C1 homologous domains and are insensitive to diacylglycerol and calcium.

Studies on the subcellular distribution of PKC isozymes demonstrate that activation of PKC results in its redistribution in the cells (also termed translocation), such that activated PKC isozymes associate with the plasma membrane, cytoskeletal elements, nuclei, and other subcellular compartments (Saito, N. et al., *Proc. Natl. Acad. Sci. USA*, 86:3409-3413 (1989); Papadopoulos, V. and Hall, P. F. *J. Cell Biol.*, 108: 553-567 (1989); Mochly-Rosen, D., et al., *Molec. Biol. Cell* (formerly *Cell Reg.*), 1:693-706, (1990)). The unique cellular functions of different PKC isozymes are determined by their subcellular location. For example, activated $β_I$PKC is found inside the nucleus, whereas activated $β_{II}$PKC is found at the perinucleus and cell periphery of cardiac myocytes (Disatnik, M. H., et al., *Exp. Cell Res.*, 210:287-297 (1994)). The localization of different PKC isozymes to different areas of the cell in turn appears due to binding of the activated isozymes to specific anchoring molecules termed Receptors for Activated C-Kinase (RACKs). RACKs are thought to function by selectively anchoring activated PKC isozymes to their respective subcellular sites. RACKs bind only fully activated PKC and are not necessarily substrates of the enzyme. Nor is the binding to RACKs mediated via the catalytic domain of the kinase (Mochly-Rosen, D., et al., *Proc. Natl. Acad. Sci. USA*, 88:3997-4000 (1991)). Translocation of PKC reflects binding of the activated enzyme to RACKs anchored to the cell particulate fraction and the binding to RACKs is required for PKC to produce its cellular responses (Mochly-Rosen, D., et al., *Science*, 268:247-251 (1995)). Inhibition of PKC binding to RACKs in vivo inhibits PKC translocation and PKC-mediated function (Johnson, J. A., et al., *J. Biol. Chem.*, 271: 24962-24966 (1996a); Ron, D., et al., *Proc. Natl. Acad. Sci. USA*, 92:492-496 (1995); Smith, B. L. and Mochly-Rosen, D., *Biochem. Biophys. Res. Commun.*, 188:1235-1240 (1992)).

In general, translocation of PKC is required for proper function of PKC isozymes. Peptides that mimic either the PKC-binding site on RACKs (Mochly-Rosen, D., et al., *J. Biol. Chem.*, 226:1466-1468 (1991a); Mochly-Rosen, D., et al., supra, 1995) or the RACK-binding site on PKC (Ron, et al., supra, 1995; Johnson, J. A., et al., supra, 1996a) are isozyme-specific translocation inhibitors of PKC that selectively inhibit the function of the enzyme in vivo.

Agents capable of decreasing or overcoming such addiction and, if possible, alleviating or removing the symptoms related to the withdrawal of habit-forming and addictive drugs are desired by both persons suffering from addiction and by society in general. Inhibitors of PKC may be a class of such agents.

SUMMARY OF THE INVENTION

In one aspect the invention includes a method for alleviating symptoms associated withdrawal from a habit-forming drug, comprising administering a peptide having isozyme-specific inhibitory activity for γPKC or εPKC.

In one embodiment, the peptide is administered prior to, during, or subsequent to delivery of the habit-forming drug.

In another embodiment, the peptide has a sequence identified herein as SEQ ID NO:1 or SEQ ID NO:2. In other embodiments, the peptide has a sequence selected from the group of sequences identified herein as SEQ ID NO:4-SEQ ID NO:14.

The peptide, in other embodiments, is formulated for intracellular delivery. For example, the peptide is conjugated to a carrier or is admixed with a formulation capable of intracellular delivery.

The habit-forming drug is an opioid, alcohol, or nicotine, in other embodiments of the invention.

In another aspect, the invention includes a method for alleviating symptoms associated withdrawal from a habit-forming drug, comprising administering a peptide having isozyme-specific activity for εPKC prior to or concurrent with delivery of the narcotic; and administering a peptide having isozyme-specific activity for γPKC subsequent to delivery of the habit-forming drug.

In one embodiment, the peptide having isozyme-specific activity for εPKC has a sequence identified herein as SEQ ID NO:1. In another embodiment, the peptide having isozyme-specific activity for γPKC has a sequence identified herein as SEQ ID NO:2.

Administration of the peptide(s) is by injection, in one embodiment.

In yet another aspect, the invention includes kit for alleviating symptoms associated withdrawal from an addictive agent, comprising (i) at least one container containing a peptide having isozyme-specific inhibitory activity for γPKC or εPCK; and (ii) instructions for use.

In one embodiment, the kit is comprised of a first container containing a peptide having isozyme-specific inhibitory activity for εPKC.

In another embodiment, the kit includes a second container containing a peptide having isozyme-specific inhibitory activity for γPKC.

The peptide in the kit, in one embodiment, has a sequence identified herein by SEQ ID NO:1 or SEQ ID NO:2.

In one embodiment, the kit's instructions direct a user to administer the peptide having isozyme-specific inhibitory activity for εPKC prior to or concurrent with administration of an addictive agent.

In another embodiment, the kit's instructions direct a user to administer the peptide having isozyme-specific inhibitory activity for γPKC after administration of an addictive agent.

In another embodiment, the kit further includes at least one syringe suitable for injecting the peptide.

An additional aspect includes the use of the peptide inhibitors in the preparation of a medicament for use in managing the withdrawal from and/or reducing the dependence on addictive drugs.

BRIEF DESCRIPTION OF THE DRAWINGS

FIGS. 1A-1C show naloxone-precipitated hyperresponsiveness of the in vitro slow ventral root potential (sVRP) of the isolated spinal cord before (FIG. 1A) and during (FIG. 1B) opioid exposure, and following treatment with naloxone, an opioid antagonist (FIG. 1C).

FIG. 5A shows the experimental protocol for the data reported in FIGS. 5B-5C where animals were treated with a PKC inhibitor prior to delivery of morphine; naloxone was administered 30 minutes after morphine delivery; and mechanical threshold and thermal response latency testing were done at 10 minute intervals after naloxone administration.

FIGS. 5B-5C are plots of average mechanical threshold, in grams, (FIG. 5B) and of average thermal response latency, in seconds, (FIG. 5C) as a function of time post application of naloxone or saline for animals treated according to the protocol shown in FIG. 5A, for animals treated with Tat-conjugated PKC ε (vertical striped bars), Tat-conjugated γ PKC (cross hatched bars), Tat carrier alone (dotted bars), or saline (open bars) administered intrathecally immediately before morphine. The dotted line represents the average baseline threshold.

FIGS. 9A-9C are traces from an NMDA-evoked current in a motor neuron before (control, FIG. 8A), during (FIG. 8B), and after (FIG. 8C) application of alcohol (EtOH) in the presence of a calcium chelating agent BAPTA (1,2-bis(2-aminophenoxy)ethane-N,N,N',N'-tetraacetic acid).

FIGS. 9D-9E are plots showing the normalized NMDA current ($I_{NMDA}$) Area as a function of time (FIG. 9D) and the NMDA current area (as a percent of control) following application of alcohol (EtOH) in the presence of BAPTA to a lumbar spinal cord slice motor neuron and following wash with artificial cerebrospinal fluid (FIG. 9E).

FIGS. 11A-11F show the results of NMDA-induced currents in spinal cord sections in the presence of alcohol and the γV5-3 PKC peptide inhibitor (SEQ ID NO:2), where FIGS. 11A, 11C, and 11F are plots of normalized NMDA current ($I_{NMDA}$) Area as a function of time before, during and after application of ethanol in the presence of 2 nM γV5-3 peptide (FIG. 11A), 5-10 nM γV5-3 peptide (FIG. 11C), and 10 nM Tat carrier peptide alone (FIG. 11E); FIGS. 11B, 11D, and 11F are histograms corresponding to FIGS. 11A, 11C, and 11F, respectively.

FIG. 14A) and of the ethanol concentration in the spinal cord (μg ethanol/mg tissue) for 7 day old (closed circles) and 21 day old rat pups (open circles) as a function of time post ethanol injection.

Figure 1D:
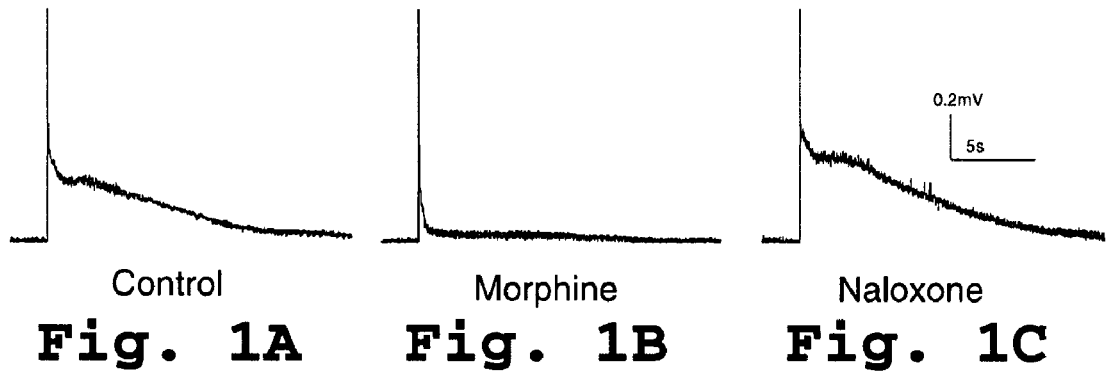
FIG. 1D is a plot of the area under the curve of the sVRP as a function of time, in minutes, to show the time course of morphine depression and naloxone-precipitated hyperresponsiveness. The bars indicate the time of application of morphine and naloxone to the isolated spinal cord.
Figure 1D:
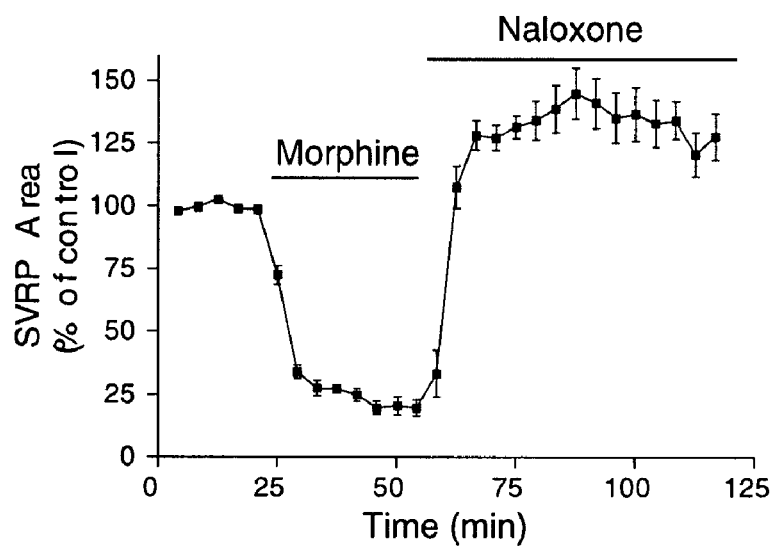

injection. At the 4 hour time point a PKC inhibitor peptide, εPKC V1-2 (SEQ ID NO:1; dotted bars) or γPKC V5-3 (SEQ ID NO:2, vertical striped bars), or Tat carrier peptide alone (SEQ ID NO:3, open bars) was administered intrathecally.

These and other objects and features of the invention will be more fully appreciated when the following detailed description of the invention is read in conjunction with the accompanying drawings.

BRIEF DESCRIPTION OF THE SEQUENCES

SEQ ID NO:1 is an εPKC antagonist peptide.
SEQ ID NO:2 is a peptide inhibitor of the γ isozyme of PKC.
SEQ ID NO:3 is a Tat-derived carrier peptide (Tat 47-57).
SEQ ID NO:4 is a modification of SEQ ID NO:2.
SEQ ID NO:5 is a modification of SEQ ID NO:2.
SEQ ID NO:6 is a modification of SEQ ID NO:2.
SEQ ID NO:7 is a modification of SEQ ID NO:2.
SEQ ID NO:8 is a modification of SEQ ID NO:2.
SEQ ID NO:9 is a modification of SEQ ID NO:2.
SEQ ID NO:10 is a modification of SEQ ID NO:2.
SEQ ID NO:11 is a modification of SEQ ID NO:2.
SEQ ID NO:12 is a modification of SEQ ID NO:2.
SEQ ID NO:13 is a modification of SEQ ID NO:2.
SEQ ID NO:14 is a modification of SEQ ID NO:2.
SEQ ID NO:15 is the *Drosophila* Antennapedia homeodomain-derived carrier peptide.

DETAILED DESCRIPTION OF THE INVENTION

I. Definitions

Abbreviations for amino acid residues are the standard 3-letter and/or 1-letter codes used in the art to refer to one of the 20 common L-amino acids.

"Conservative amino acid substitutions" are substitutions which do not result in a significant change in the activity or tertiary structure of a selected polypeptide or protein. Such substitutions typically involve replacing a selected amino acid residue with a different residue having similar physicochemical properties. For example, substitution of Glu for Asp is considered a conservative substitution since both are similarly-sized negatively-charged amino acids. Groupings of amino acids by physico-chemical properties are known to those of skill in the art.

"Peptide" and "polypeptide" are used interchangeably herein and refer to a compound made up of a chain of amino acid residues linked by peptide bonds. Unless otherwise indicated, the sequence for peptides is given in the order from the amino terminus to the carboxyl terminus.

The term "narcotic" as used herein intends the meaning set forth in standard medical reference works, such as the "more recent" definitions used in Stedman's Medical Dictionary, 26th edition (Williams & Wilkins Publ., Baltimore, 1995) and in the "Analgesics" chapter in the "Drug Evaluations" subscription service published by the American Medical Association (Chicago). Briefly, "narcotics" as used in any definition (either classical or recent) includes: (1) opiate drugs, defined as any preparation or derivative of opium, a natural mixture derived from poppy plants that includes a number of medically important and/or habit-forming or addictive drugs, including morphine, codeine, noscapine, papaverine, thebaine, and heroin; and, (2) opioid drugs, which includes opiates as well as various synthetic narcotic drugs having similar or related chemical structures and effects. Exemplary synthetic narcotics include (DEMEROL™), hydrocodone (VI-CODIN™), hydromorphone (DILAUDID™), propoxyphene (DARVON™), oxycodone (PERCODAN™ when mixed with aspirin, or PERCOCET™ when mixed with acetaminophen), levorphanol, fentanyl, and methadone.

A drug is typically classified as a "narcotic", if its effects include: (1) the ability to induce "significant alteration of mood and behavior"; (2) the ability to induce a condition of "stuporous analgesia"; and (3) a substantial risk of dependence, tolerance, and/or addiction.

More generally, "habit-forming drugs" as used herein refer to various agents such as alcohol; minor tranquilizers such as barbiturates, e.g. pentobarbital, and benzodiazepines, e.g. librium, valium; stimulantia, e.g. cocaine, amphetamines and nicotine; narcotics, including opiates, such as fentanyl, alfentanyl and heroine; and hallucinogens, such as LSD; either in pure form or in admixture; tobacco; hashish; marijuana; and the like.

Individuals suffering from an "addiction" are identified by, for example, the presence of any one or more of a number of undesired symptoms upon abstinence of the drug. Typical symptoms accompanying withdrawal or abstention of habit-forming drugs can include a general feeling of discomfort, headache, tremor, anxiety, hallucinations, nausea, vomiting and the like, and in particular a continuous desire or longing for the habit-forming drug having caused the addiction.

"Managing, attenuating, or alleviating the symptoms of withdrawal" intends a perceptible reduction by the subject in one or more of the symptoms associated with drawal from a particular addictive agent, including but not limited to symptoms of allodynia (nociceptive response to a normally innocuous stimulus), hyperalgesia (exaggerated response to a noxious stimulus), headache, tremor, anxiety, hallucinations, nausea, vomiting, and a continuous desire or longing for the habit-forming drug having caused the addiction.

II. Compositions and Methods for Managing Withdrawal

The present invention is premised upon the discovery that ε and γ protein kinase C are involved in the mechanism of withdrawal from habit-forming and addictive drugs, and that their selective inhibition can alleviate or remove the symptoms related to withdrawal.

1. Morphine Withdrawal

The slow ventral root potential (sVRP) is an electrophysiolgical measurement of nociceptive-related response in the spinal cord lasting approximately 40 seconds (Yanagisawa et al., *Eur. J. Pharmacol.,* 106:231-239 (1984); Akagi H. et al., *British J. Pharmacol.,* 84:663-673 (1985); Otsuka M. et al., *J. Physiol.,* 395:255-270 (1988)). It is evoked by stimulation of a lumbar dorsal root at an intensity sufficient to activate small diameter afferents that transmit nociceptive (painful) stimuli from the periphery to the spinal cord (Lozier A. P. et al., *J. Neurophysiol.,* 74:1001-1009 (1995)). Isolated spinal cords can be used to characterize the in vitro nociceptive hyperresponsiveness of opiate withdrawal since in this model withdrawal to opioids is displayed as an increase in the nociceptive-related slow ventral root potential (sVRP) to a level above control when, for example, the μ-opioid receptor agonist morphine is followed by administration of the opioid antagonist naloxone. Thus, the sVRP is related to pain, and its exaggeration following naloxone is a manifestation of withdrawal which translates to an increase in pain sensation in vivo.

As described in Example 1, neonatal rat spinal cords were isolated from 5-7 day old rats and arranged for measurement of sVRP. FIGS. 1A-1C show the initial sVRP (FIG. 1A) of the isolated spinal cords, during exposure to morphine (FIG. 1B) and then to naloxone (FIG. 1C). The sVRP is depressed by morphine and recovers to levels significantly above control on administration of naloxone. Thirty min following the application of naloxone the area of the sVRP was 140.9% of control ±10.12 (mean±SEM) (P<0.001). The hyperresponsiveness persisted for at least an hour.

FIG. 1D shows the time course of morphine depression and naloxone-precipitated hyperresponsiveness by plotting the area under the curve of each individual sVRP trace as a function of time, in minutes. The bars indicate the time of application of morphine and naloxone to the isolated spinal cord. The depression in sVRP due to administration of morphine and the hyperresponsiveness upon application of naloxone is apparent.

Figure 2A:
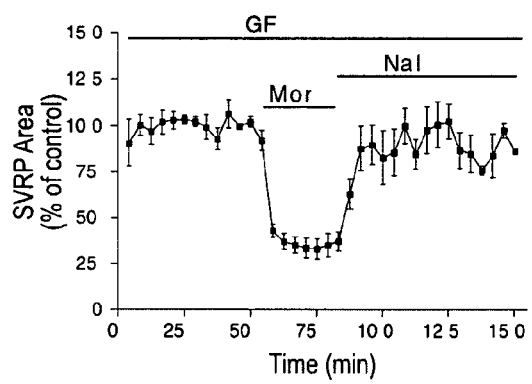
FIGS. 2A-2D are plots showing the area under the curve of the slow ventral root potential (sVRP) as a function of time, in minutes, following application of various non-specific PKC inhibitors: the broad spectrum inhibitor GF109203X in the presence (FIG. 2A) and absence (FIG. 2C) of morphine; and an inhibitor specific to $Ca^{++}$-dependent PKC isoforms, Go6976 in the presence (FIG. 2B) and absence (FIG. 2D) of morphine.
Figure 2B:
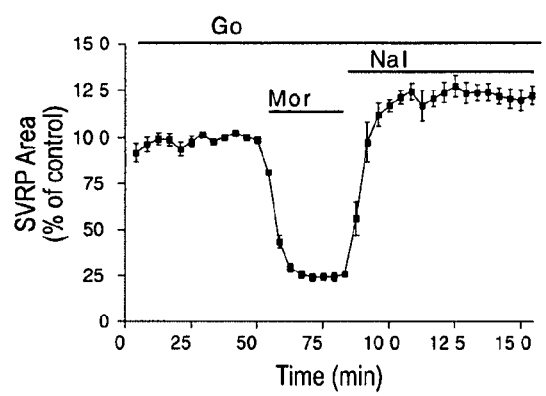
Figure 2C:
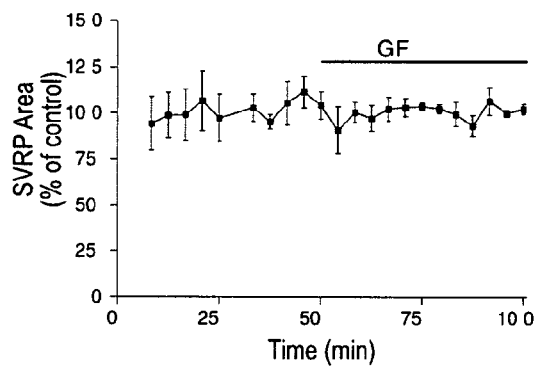
Figure 2D:
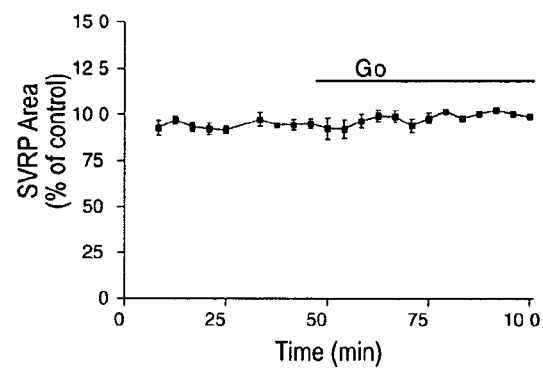

Having established the use and validity of this model for characterizing the naloxone-precipitated nociceptive response, the effect of various PKC antagonists/inhibitors on the hyperresponsiveness was evaluated. FIGS. 2A-2D are plots showing the slow ventral root potential (sVRP) as a function of time, in minutes, following application of various non-specific PKC inhibitors: the broad spectrum inhibitor GF109203X in the presence (FIG. 2A) and absence (FIG. 2C) of morphine; and an inhibitor specific to $Ca^{++}$-dependent PKC isoforms, Go6976 in the presence (FIG. 2B) and absence (FIG. 2D) of morphine. The PKC antagonist GF109203X blocked the withdrawal hyperresponsiveness (FIG. 2A), as evidenced by the result that at 30 minutes following naloxone sVRP area was 87% (±9.8%) of control. This was not significantly different from control but was significantly different from the exaggerated response following naloxone without the antagonist. The PKC antagonist Go6976 did not block withdrawal (FIG. 2B) since mean sVRP area 30 minutes after naloxone was 127.4% (±5.5%) of control, a value not significantly different from naloxone alone. Neither inhibitor alone altered the sVRP (FIGS. 2C-2D).

Figure 3A:
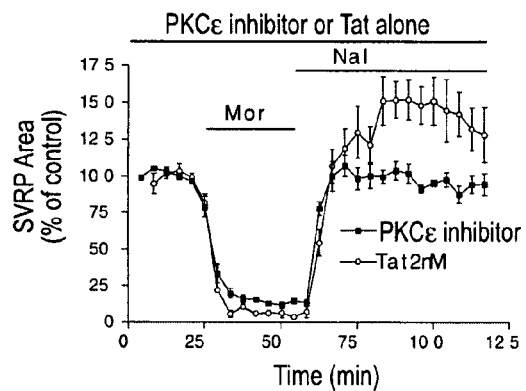
FIGS. 3A-3B are plots showing the area under the curve of the slow ventral root potential (sVRP) as a function of time, in minutes, following application of morphine and naloxone in the presence of Tat-conjugated PKC ε-specific peptide inhibitor εV1-2 (FIG. 3A, closed squares) or Tat alone (FIG. 3A, open circles); and following application of the Tat-conjugated PKC ε inhibitor alone in the absence of morphine (FIG. 3B).
Figure 3B:
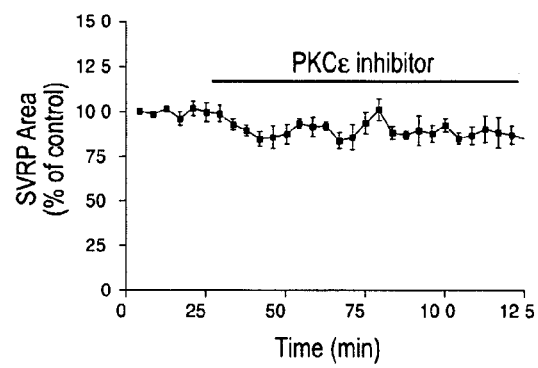
Figure 6A:
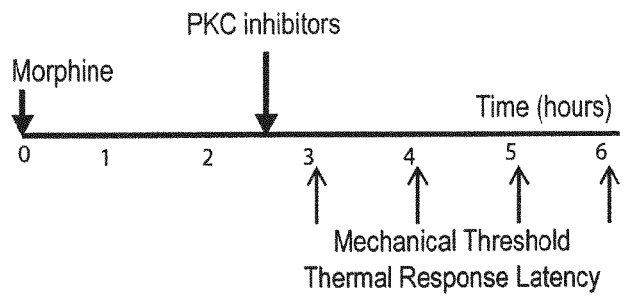
FIG. 6A shows the experimental protocol for the data reported in FIGS. 6B-6C where animals were treated with a PKC inhibitor 2.5 hours subsequent to delivery of morphine; and mechanical threshold and thermal response latency testing were done at hourly intervals after peptide administration.
Figure 6B:
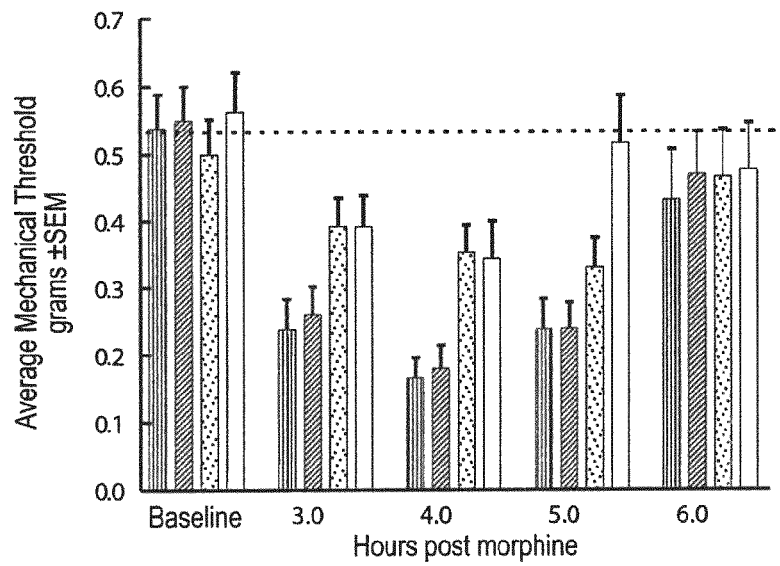
FIGS. 6B-6C are plots of average mechanical threshold, in grams, (FIG. 6B) and of average thermal response latency, in seconds, (FIG. 6C) as a function of time post application of morphine for animals treated according to the protocol shown in FIG. 5A, for animals treated with Tat-conjugated PKC ε (vertical striped bars), Tat-conjugated γ PKC (cross hatched bars), Tat carrier alone (dotted bars), or saline (open bars) administered intrathecally immediately before morphine. The dotted line represents the average baseline threshold.

In another study conducted according to the procedure set forth in Example 1, the PKC isozyme specific antagonists εPKC V1-2 (SEQ ID NO:1) and γPKC V5-3 (SEQ ID NO:2) were applied to the isolated spinal cords. The results for the εPKC antagonist are shown in FIGS. 3A-3B. FIG. 3A shows the slow ventral root potential (sVRP) area as a function of time following application of morphine and naloxone in the presence of Tat-conjugated PKC ε-specific peptide inhibitor εV1-2 (closed squares) or Tat alone (open circles; SEQ ID NO:3). The Tat-conjugated εPKC V1-2 peptide blocked withdrawal hyperresponsiveness, as seen by the result that sVRP area 30 minutes after naloxone administration was 102% of control. In contrast, the Tat peptide alone (open circles) did not block the withdrawal response. FIG. 6B shows that in the absence of morphine εPKC V1-2 did not alter the sVRP.

Figure 3C:
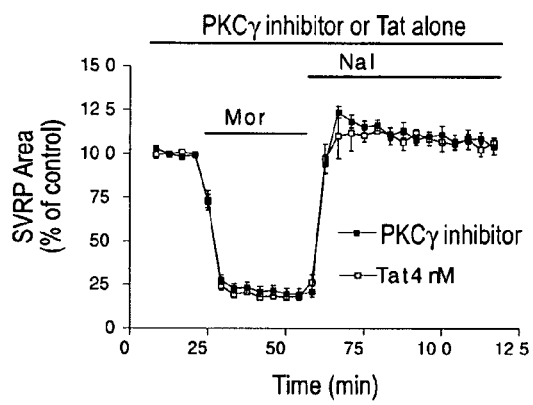
FIGS. 3C-3D are plots showing the area under the curve of the slow ventral root potential (sVRP) as a function of time, in minutes, following application of morphine and naloxone in the presence of Tat-conjugated PKC γ isozyme-specific antagonist γV5-3 (FIG. 3C, closed squares) or Tat carrier alone (FIG. 3C, open circles); and following application of the Tat-conjugated γPKC antagonist γV5-3 in the absence of morphine (FIG. 3D).
Figure 3D:
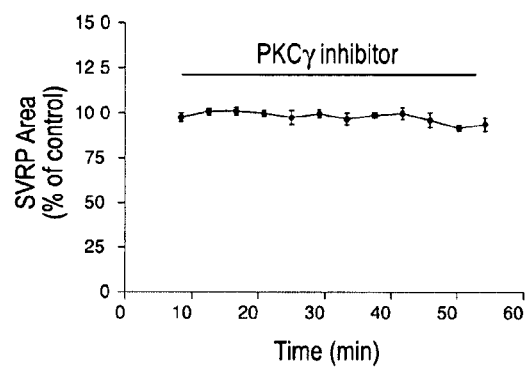
Figure 6C:
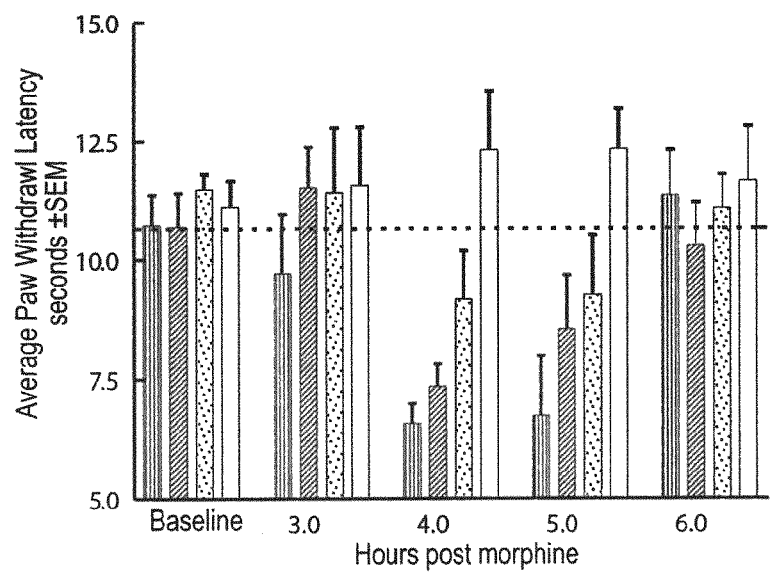

The results for administration of the γPKC antagonist γV5-3 are shown in FIGS. 3C-3D. γPKC V5-3 (closed squares) reduced withdrawal hyperresponsiveness, but not to a significantly greater amount than the Tat carrier vehicle alone (open circles; FIG. 6C) suggesting that the apparent reduction in withdrawal associated with the PKC γ inhibitor is due to the Tat carrier peptide. This finding agrees with the non-specific inhibitor findings that the global PKC antagonist GF109293X (FIG. 2A), but not a Ca2+ dependent antagonist Go6976 (FIG. 2B), blocked withdrawal hyperreponsiveness following a 30 minute exposure to morphine. FIG. 3D shows that in the absence of morphine and naloxone, γPKC V5-3 did not significantly altered the sVRP.

In another group of animals, the effect of the non-specific PKC antagonist chelerythrine was studied. Chelerythrine administered to morphine-exposed spinal cords did not alter the response to morphine (results not shown). However, chelerythrine did block morphine withdrawal, as evidenced by the sVRP response following naloxone in combination with chelerythrine of 100.1% of control (data not shown).

These studies demonstrate that naloxone-precipitated withdrawal hyperresponsiveness in the spinal cord requires activation of εPCK. In isolated spinal cords subject to a brief morphine exposure in vitro PKC inhibitors specific for εPKC prevented the increase in sVRP that follows naloxone treatment. As will be shown below from the in vivo studies, morphine withdrawal also involves the γ isozyme of PKC, but at different time points than used in the in vitro studies.

Figure 4A:
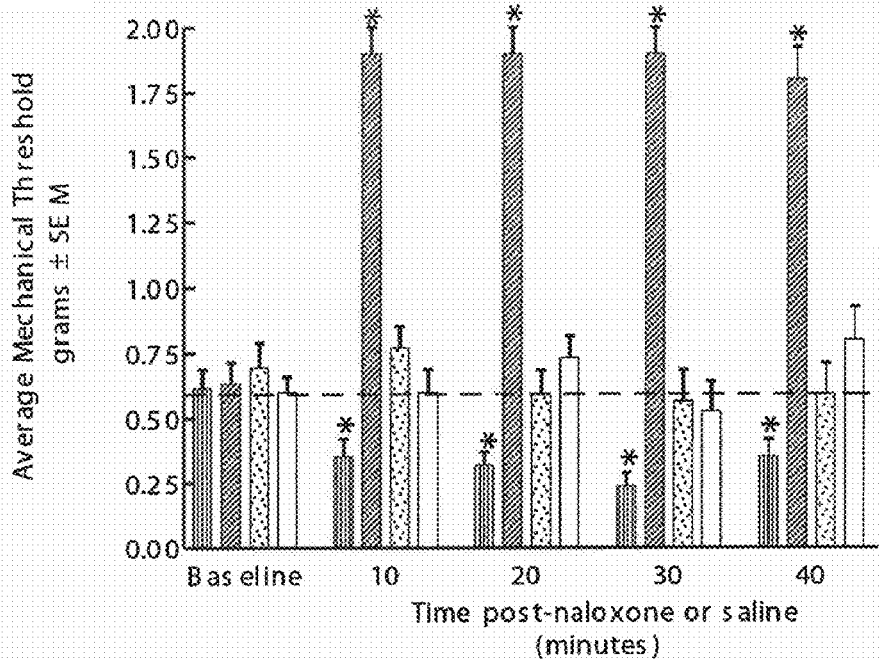
FIGS. 4A-4B are plots of average mechanical threshold, in grams, (FIG. 4A) and of average thermal response latency, in seconds, (FIG. 4B) as a function of time post application of naloxone or saline. Naloxone or saline (vertical striped bars and cross-hatched bars, respectively) was administered 30 minutes after delivery of morphine to postnatal day 7 rats. Naloxone or saline (dotted bars and open bars) were administered to animals not treated with morphine as controls. The dotted line represents the average baseline mechanical threshold.
Figure 4B:
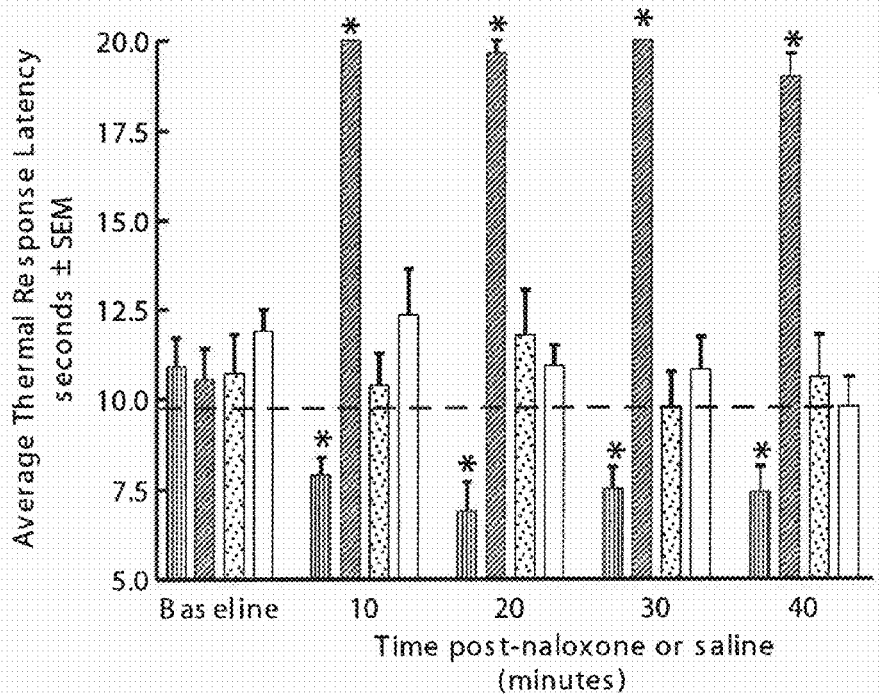

In vivo studies on opiate withdrawal allodynia and hyperalgesia were conducted using postnatal day 7 rats. As described in Example 2, postnatal day 7 rats were given morphine subcutaneously followed 30 minutes later by naloxone or saline. Mechanical threshold using von Frey filaments to produce the flexion withdrawal response of the hind paw and thermal stimulation to measure the paw withdrawal latency were measured as described in Example 2. FIG. 4A shows the results of the mechanical threshold test and FIG. 4B shows the results of the thermal paw withdrawal latency test. Neonatal rats given morphine exhibited profound analgesia manifested as increased paw withdrawal thresholds to increasing mechanical pressure using von Frey filaments and increased paw withdrawal latency to thermal stimulation (cross hatched bars, FIGS. 4A-4B). Administration of the opioid antagonist naloxone following 30 minutes of morphine exposure (vertical-striped bars) precipitated mechanical allodynia and thermal hyperalgesia, manifested as decreased mechanical threshold or a shorter paw withdrawal latency, respectively, compared to baseline pre-morphine measures (e.g., increased pain sensitivity to both noxious and non-noxious stimuli upon withdrawal from morphine). Naloxone alone (dotted bars) did not alter paw withdrawal thresholds to mechanical stimulation or paw withdrawal latency to thermal stimulation.

FIG. 5A illustrates a treatment protocol where rat pups were given a PKC antagonist intrathecally (e.g., directly into the cerebrospinal fluid surrounding the spinal cord) prior to subcutaneous morphine delivery. Thirty minutes after morphine delivery, naloxone was administered, followed by mechanical allodynia and thermal hyperalgesia testing (as described in Example 2). The results are shown in FIGS. 5B-5C.

FIG. 5B shows the average mechanical threshold, in grams, as a function of time post application of naloxone saline for animals treated according to the protocol shown in FIG. 5A with εPKC V1-2 (SEQ ID NO:1; vertical-striped bars), γPKC V5-3 (SEQ ID NO:2; cross-hatched bars), Tat carrier alone (SEQ ID NO:3; dotted bars) or saline (open bars). FIG. 5C is a similar plot for the average thermal response latency test. The data shows that Tat-conjugated PKC εV1-2 (vertical-striped bars) administered prior to morphine delivery was effective to block naloxone-precipitated morphine withdrawal allodyina and hyperalgesia (e.g., PKC ε mediates withdrawal induced sensitization of pain pathways). Pretreatment with Tat-conjugated γPKC V5-3 (cross-hatched bars) had a smaller blocking effect. The Tat carrier alone (dotted bars) and saline (open bars) did not prevent allodynia and hyperalgesia.

Another study was performed to investigate the roles of PKC isozymes in natural withdrawal, which more closely resembles the clinical setting in addictive sequela. In this study, postnatal day 7 rats were given a single injection of morphine (1 mg/kg) and allowed to undergo natural withdrawal, i.e., naloxone was not administered to precipitate withdrawal. The treatment protocol is shown in FIG. 6A, where 2.5 hours after morphine delivery, εV1-2 or γV5-3 peptide inhibitors were administered intrathecally. Mechanical allodynia and thermal hyperalgesia were evaluated at hourly intervals according to the procedure described in Example 2. The results are shown in FIGS. 6B-6C.

FIG. 6B shows the results for the mechanical threshold test and of FIG. 6C shows the results of the thermal response latency. Animals were treated with Tat-conjugated PKC ε (SEQ ID NO:1; vertical-striped bars), Tat-conjugated γ PKC (SEQ ID NO:2, cross hatched bars), Tat carrier alone (SEQ ID NO:3, dotted bars), or saline (open bars), each administered intrathecally immediately before morphine delivery. The rats developed mechanical allodynia and thermal hyperalgesia as a result of withdrawal (see saline treated animals, open bars). Administration of γV5-3 (cross-hatched bars) attenuated mechanical allodynia and thermal hyperalgesia during natural withdrawal from morphine ($p<0.05$ for γV5-3 versus Tat carrier alone (dotted bars) or saline (open bars)).

The data in FIGS. 5-6 show a temporal relationship of the PKC isozymes ε and γ in blocking the in vivo withdrawal response. εPKC peptide antagonists were effective to prevent naloxone-precipitated mechanical allodynia and thermal hypersensitivity in vivo and the exaggerated nociceptive spinal response in vitro due to morphine exposure. The εV1-2 peptide was most effective when administered prior to morphine exposure. γPKC peptide antagonists were effective to attenuate the withdrawal symptoms when administered after morphine exposure, and were most effective after a longer morphine exposure time (FIGS. 6B-6C). From this temporal relationship, morphine exposure appears to produce an early phase of PKC ε-dependent primary afferent sensitization leading to an increase in transmitter release, followed by a later phase involving PKC γ-dependent spinal sensitization.

Thus, the invention contemplates administration of an cPKC antagonist or a γPKC antagonist for management of opioid withdrawal hyperalgesia in a subject. In particular, an εPKC antagonist can be administered prior to, concurrent with, or shortly after delivery of the opioid to alleviate the allodynia and hyperalgesia associated withdrawal. A γPKC antagonist is preferably administered subsequent to opioid delivery, and most preferably an hour or more after opioid delivery, to alleviate the allodynia and hyperalgesia associated withdrawal. A combination therapy is also contemplated, where an εPKC antagonist is administered prior to, concurrent with, or shortly after delivery of the opioid followed by delivery of a γPKC antagonist after delivery of the opioid. That is, if the εPKC antagonist is administered shortly after opioid delivery, the γPKC antagonist can be administered concurrent with the cPKC antagonist or subsequent to administration of the εPKC antagonist.

2. Alcohol Withdrawal

Alcohol withdrawal symptoms contribute to addiction to alcohol (alcoholism) and pose a serious clinical problem. Studies were performed to demonstrate the ability of peptides specific for the ε and γ isozymes of PKC to alleviate the symptoms of withdrawal from alcohol. The studies included characterizing the ability of γPKC peptides to mediate alcohol withdrawal hyperresponsiveness of N-methyl-D-aspartate (NMDA) receptor currents mediated by glutamatergic neurotransmission in neonatal rat spinal cord motor neurons and the ability of εPKC and γPKC peptide inhibitors to attenuate withdrawal symptoms in young rats. These studies will now be described.

a. In Vitro Studies

Figure 7A:
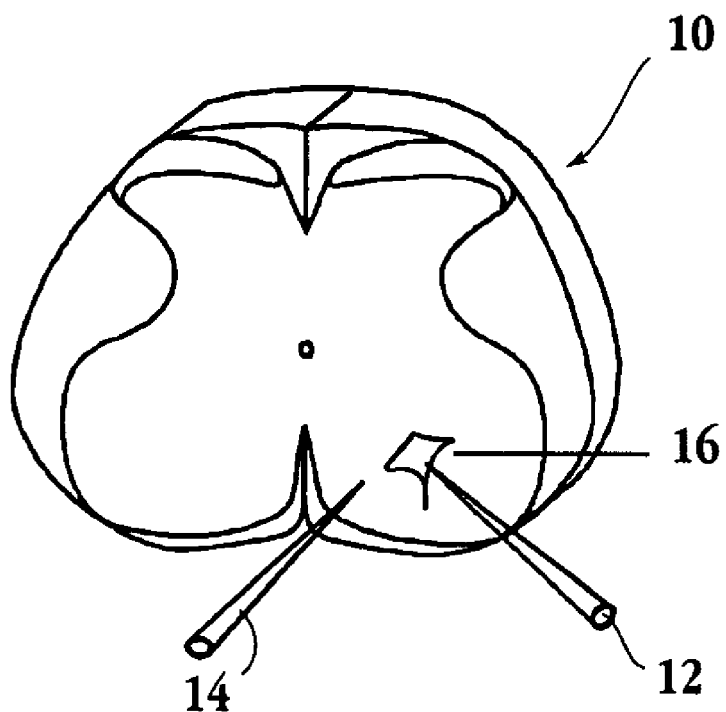
FIG. 7A is a schematic diagram of a lumbar spinal cord slice for testing of alcohol-induced withdrawal hyperresponsiveness in N-methyl-D-aspartate (NMDA) receptor currents.
Figure 7B:
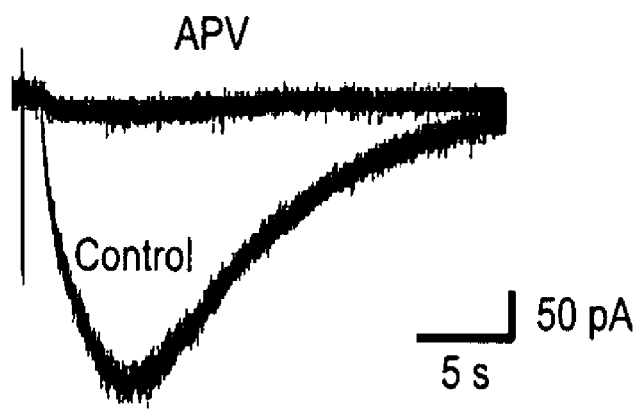
FIG. 7B shows an individual trace elicited from a lumbar spinal cord slice motor neuron before (control) and after application of the NMDA antagonist 2-amino-5-phosphonovaleric acid (APV).

Spinal cords were taken from young rats, and slices of these cords were made and placed in artificial cerebrospinal fluid for patch clamp electrophysiological analysis, to characterize the ability of γPKC peptides to mediate alcohol withdrawal hyperresponsiveness of N-methyl-D-aspartate (NMDA) receptor currents. FIG. 7A is a schematic diagram of the technique, where a lumbar spinal cord slice 10 is shown. The placement of a recording electrode 12 and a pipette 14 for application of NMDA relative to a motor neuron 16 is illustrated. FIG. 7B shows an individual trace elicited from the cord slice motor neuron before (control) and after application of the NMDA antagonist 2-amino-5-phosphonovaleric acid (APV).

Figures 8A, 8B, 8C:
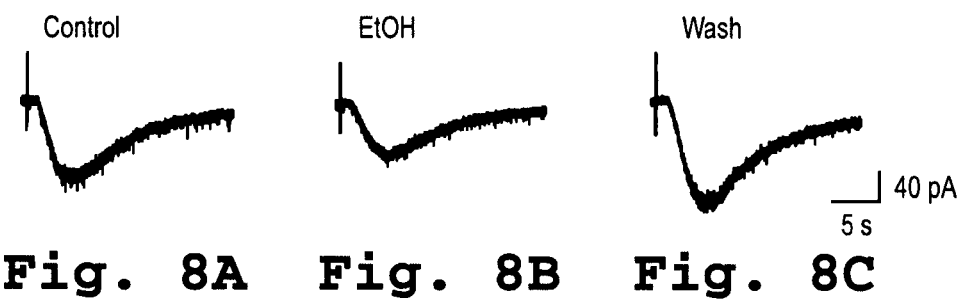
FIG. 8A-8C are traces from an NMDA-evoked current in a motor neuron before (control, FIG. 8A), during (FIG. 8B), and after (FIG. 8C) alcohol-induced withdrawal.
Figure 8D:
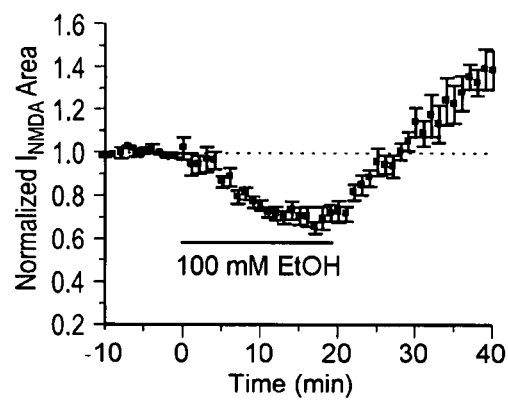
FIGS. 8D-8E are plots showing the normalized NMDA current ($I_{NMDA}$) Area as a function of time (FIG. 8D) and the NMDA current area (as a percent of control) following application of alcohol (EtOH) to a lumbar spinal cord slice motor neuron and following wash with artificial cerebrospinal fluid (FIG. 8E).

FIG. 8A-8C are traces from an NMDA-evoked current in a motor neuron before (control, FIG. 8A), during (FIG. 8B), and after (FIG. 8C) alcohol-induced withdrawal. The time-course of the effect of alcohol (EtOH) on the area of NMDA-evoked currents is shown in FIG. 8D, where the bar in the figure denotes the time of alcohol application. The normalized NMDA current ($I_{NMDA}$) area increases after application of alcohol (EtOH) to lumbar spinal cord slice motor neurons (n=11).

Figure 8E:
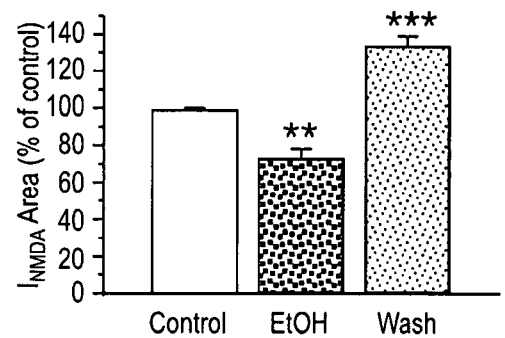

FIG. 8E is a histogram showing withdrawal hyperresponsiveness of the same lumbar spinal cord slice motor neurons (n=11) as in FIG. 8D. The NMDA-induced currents were measured 18 minutes after alcohol (100 mM) and wash (artificial cerebrospinal fluid) were applied. The increase in NMDA-induced current over the control level following application of ethanol is indicative of ethanol-induced withdrawal hyperresponsiveness.

The ethanol withdrawal hyperresponsiveness is calcium dependent, as shown by the data presented in FIGS. 9A-9E. FIGS. 9A-9C are traces from an NMDA-evoked current in a motor neuron before (control, FIG. 8A), during (FIG. 8B), and after (FIG. 8C) application of alcohol (EtOH) in the presence of a calcium chelating agent BAPTA (1,2-bis(2-aminophenoxy)ethane-N,N,N',N'-tetraacetic acid). The individual traces from a motor neuron show no ethanol-withdrawal hyperresponsiveness when the recording pipette contains 30 mM of the calcium chelating agent BAPTA. FIG. 9D shows the time course of the mean effects of ethanol on the area of NMDA-evoked currents (n=8) in the presence of intracellular BAPTA. The bar indicates the time period of application of ethanol, and as seen, after cessation of ethanol application, the current returned to the control level. FIG. 9E is a histogram showing that in the presence of a calcium chelating agent, hyperreponsiveness subsequent to ethanol administration is not observed.

Fluorescence immunocytochemical studies were performed on the spinal cord sections, as described in Example 3. The sections were incubated with an anti-γPKC antibody and an anti-neuronal antibody to identify neurons. After washing the sections were labeled with fluorescein-labeled secondary antibodies and observed via laser confocal microscopy. While not shown here, visualization of the spinal cord sections showed an abundance of γPKC in ventral horn neurons and that ethanol reversibly induced translocation of γPKC from the nucleus to the cytoplasm. Translocation of γPKC was quantified by counting the number of cells with γPKC localized to the nucleus before (control) and after application of ethanol, as well as after washing with artificial cerebrospinal fluid. Translocation in the presence of the γPKC isozyme-specific peptide V5-3 (SEQ ID NO:2) was also evaluated by administering the γPKC V5-3 peptide to the sections and, 20 minutes later, administering ethanol. Two to three sections per animal were counted. The results are shown in FIG. 10.

Figure 10:
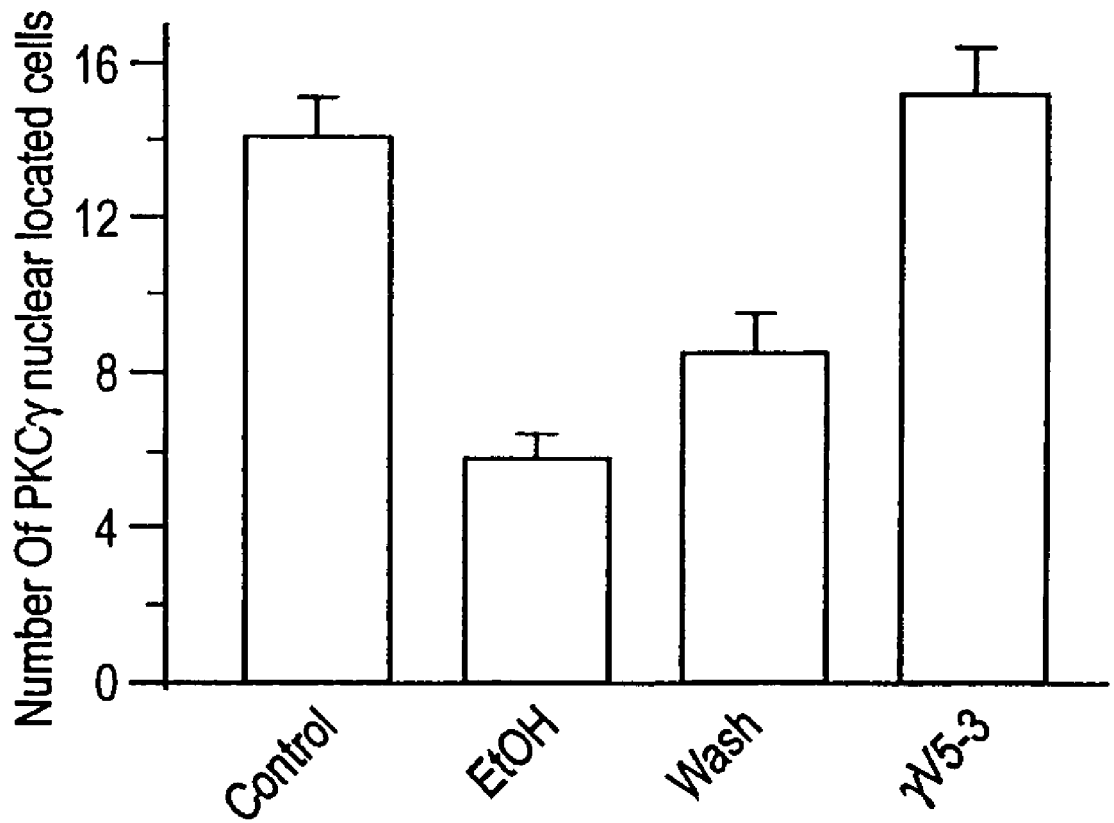
FIG. 10 is a bar graph showing the number of cells having γPKC localized in the nucleus before (control) application of ethanol, after ethanol application, after washing with artificial cerebrospinal fluid, and in the presence of γPKC V5-3 peptide inhibitor.

FIG. 10 is a bar graph showing the number of cells having γPKC localized in the nucleus. As seen, prior to ethanol application, about 14 cells were counted as having γPKC localized in the nucleus. After application of ethanol to the spinal cord sections, the number of cells having γPKC localized in the nucleus decreased to about 6, consistent with the visual observation that ethanol induced translocation of γPKC from the nucleus to the cytoplasm. The translocation was reversible, as evidenced by the increase in cells having γPKC localized in the nucleus following wash with artificial cerebrospinal fluid. The presence of γPKC isozyme-specific peptide V5-3 (SEQ ID NO:2), applied prior to ethanol exposure, was effective to block γPKC translocation to the cytoplasm, as evidenced by the number of cells having γPKC in the nucleus remaining at the control value of about 14.

FIGS. 11A-11F show the results of NMDA-induced currents in spinal cord sections in the presence of alcohol and the γV5-3 PKC peptide inhibitor (SEQ ID NO:2). FIGS. 11A-11B show the effect of ethanol on NMDA-evoked currents in the presence of 2 nm γPKC V5-3 (SEQ ID NO:2). FIG. 11A is a plot of the normalized NMDA-induced current area as a function of time, where the bar indicates the 15 minute time period for application of ethanol (100 mM). After ethanol application, the spinal cord section was washed with artificial cerebrospinal fluid. FIG. 11B is the corresponding histogram. At a dose of 2 nM, the γPKC peptide inhibitor V5-3 did not completely block withdrawal hyperresponsiveness. However, at a dose of 5-10 nM, the peptide effectively blocked ethanol withdrawal hyperresponsiveness, as seen by the data presented in FIGS. 11C-11D. FIGS. 11E-11F shows the effect of 10 nM Tat carrier alone on ethanol withdrawal hyperresponsiveness, where it is seen that the carrier peptide does not prevent the symptom.

In summary, the data in FIGS. 7-11 show that ethanol withdrawal hyperresponsiveness of NMDA-evoked currents is a calcium dependent phenomenon γPKC is a calcium-dependent isozyme. Neonatal rat spinal cord ventral horn displays abundant γPKC isozyme which is activated by ethanol to translocate from the nucleus to the cytoplasm. A γPKC isozyme specific peptide, such as SEQ ID NO:2, is effective to block the translocation, thus attenuating or blocking the ethanol withdrawal hyperresponsiveness.

b. In Vivo Studies

In vivo studies were conducted using young rats to determine the effect of peptides specific for the ε and γ PKC isozymes on ethanol withdrawal-induced allodynia and hyperalgesia. As detailed in Example 4, 7 day old and 21 day old rats were given ethanol by intraperitoneal injection. The rats were subjected to mechanical allodynia testing (von Frey hair stimulation) and thermal hyperalgesia (thermal paw withdrawal latencies) at defined intervals after ethanol administration. A baseline test was conducted prior to ethanol treatment to establish a zero time value.

Figure 12A:
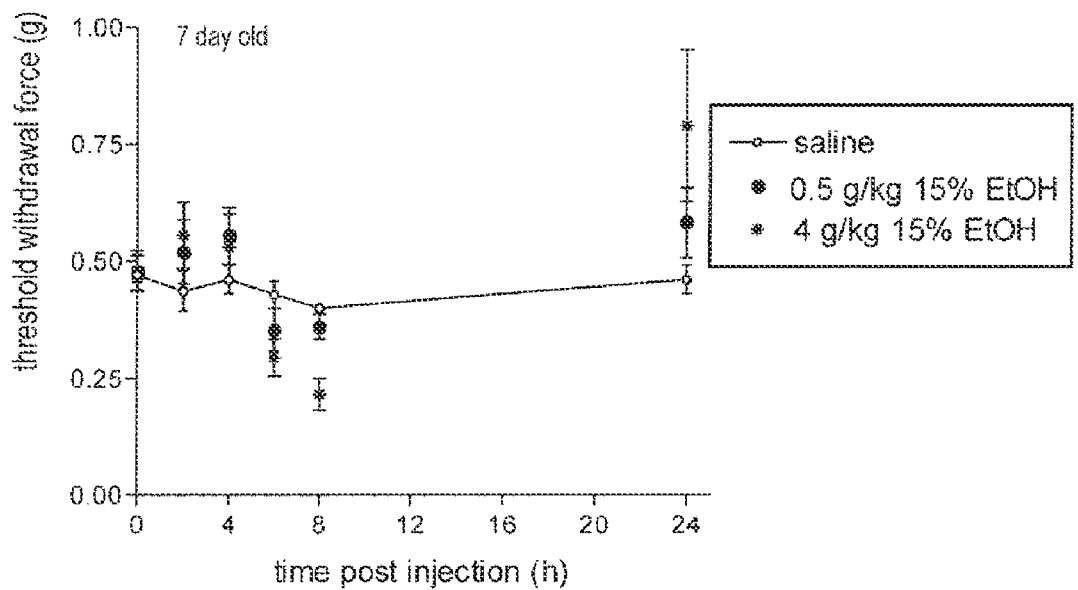
FIGS. 12A-12B are plots showing the threshold withdrawal force, in grams, as a function of time post injection of ethanol, in hours, at 0.5 g/kg (closed circles) and at 4 g/kg (stars) or post injection of saline (open circles) for 7 day old (FIG. 12A) and 21 day old (FIG. 12B) rat pups.
Figure 12B:
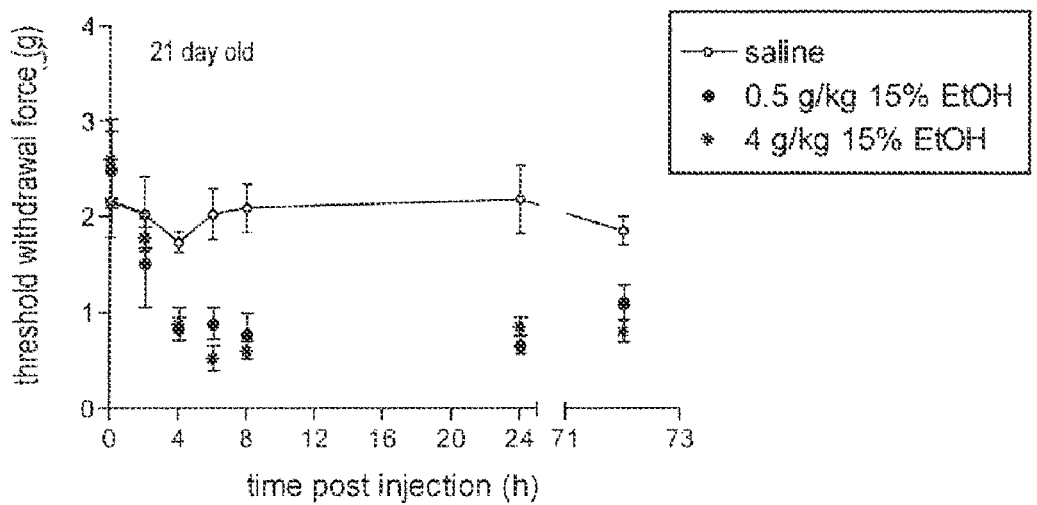

The results for the mechanical allodynia testing are shown in FIGS. 12A-12B for 7 day old pups (FIG. 12A) and 21 day old pups (FIG. 12B). The threshold withdrawal force in grams on the y-axis is defined as the log of 10 times the force in milligrams required to bend the von Frey fiber. Postnatal day 7 rats, treated with 4 g/kg 15% EtOH (star symbols), exhibited a slight but insignificant increase in threshold withdrawal force (e.g., analgesia) at the two hour test interval. At 6 hours and 8 hours post-ethanol injection the 7 day old rats exhibited mechanical allodynia as manifested by a decrease in paw threshold withdrawal force compared to saline controls (FIG. 12A). Administration of 1 g/kg 15% EtOH (closed squares) did not significantly alter the threshold withdrawal force. Baseline threshold withdrawal force, as established using pups injected with saline (open circles), remained constant for the duration of the study.

In contrast to 7 day old pups, 21 day old rats did not exhibit an increase in threshold withdrawal force (e.g., analgesia) following EtOH administration, as shown in FIG. 12B. Threshold withdrawal forces decreased as early as 4 hours and remained below baseline up to 72 hours post-ethanol injection. Administration of both high (4 g/kg; star symbols) and low (0.5 g/kg; closed circles) doses of 15% EtOH maximally decreased mechanical thresholds at 6 hours post EtOH injection. For both concentrations, withdrawal thresholds remained consistently below baseline for up to 72 hours post injection. Baseline threshold withdrawal forces in P21 rats, as established using rats injected with saline (open circles), remained constant for the duration of the study.

Figure 13A:
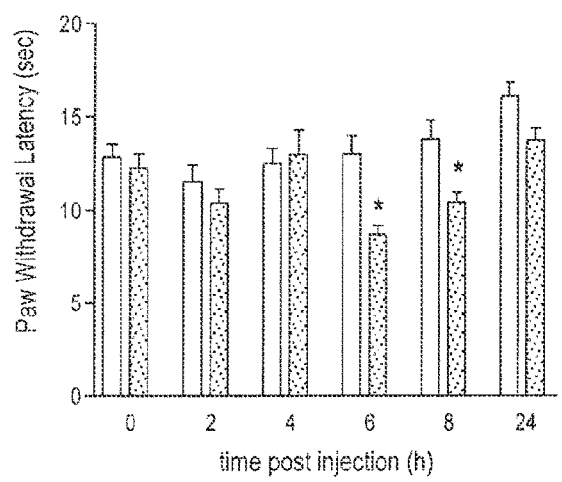
FIGS. 13A-13B are bar graphs showing the thermal paw withdrawal latencies in 7 day old rat pups (FIG. 13A) and 21 day old rat pups (FIG. 13B) exposed to a single dose of ethanol (dotted bars) or to saline (control, open bars).
Figure 13B:
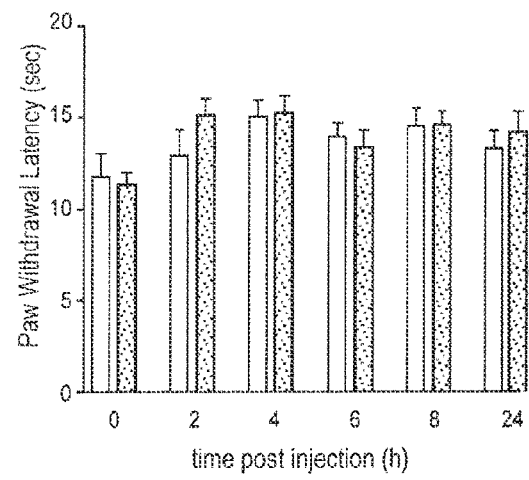

FIGS. 13A-13B shows the results of the thermal paw withdrawal latency tests for postnatal day 7 rats (FIG. 13A) and postnatal day 21 rats (FIG. 13B) treated with saline (open bars) with 4 g/kg 15% EtOH (dotted bars). The baseline thermal paw withdrawal latencies were similar in the 7 day old and 21 day old rats, at values of 12.86±0.70 and 12.26±0.79 s, respectively. Thermal hyperalgesia as evidenced by a decrease in paw withdrawal latency, was observed in the 7 day old rats at 6 hours following administration of 4 g/kg 15% EtOH (FIG. 13A). No change in paw withdrawal latencies were observed in saline controls. In contrast to the 7 day old rats, 21 day old rats administered 4 g/kg 15% EtOH did not exhibit a decrease in paw withdrawal latency as compared to saline controls over the entire time period examined (FIG. 13B). No change in paw withdrawal latencies were observed in the saline-control 21 day old pups.

To determine if mechanical allodynia and thermal hyperalgesia correlated temporally with decreases in EtOH concentrations and to determine if the observed difference in response between 7 day old and 21 day old rats was due to different EtOH pharmacokinetics, blood and spinal cord EtOH concentrations following a single 4 g/kg 15% EtOH administration were measured. Blood and spinal cord ethanol levels were determine according to the procedure described in Example 4. The results are shown in FIGS. 14A-14B.

Figure 14A:
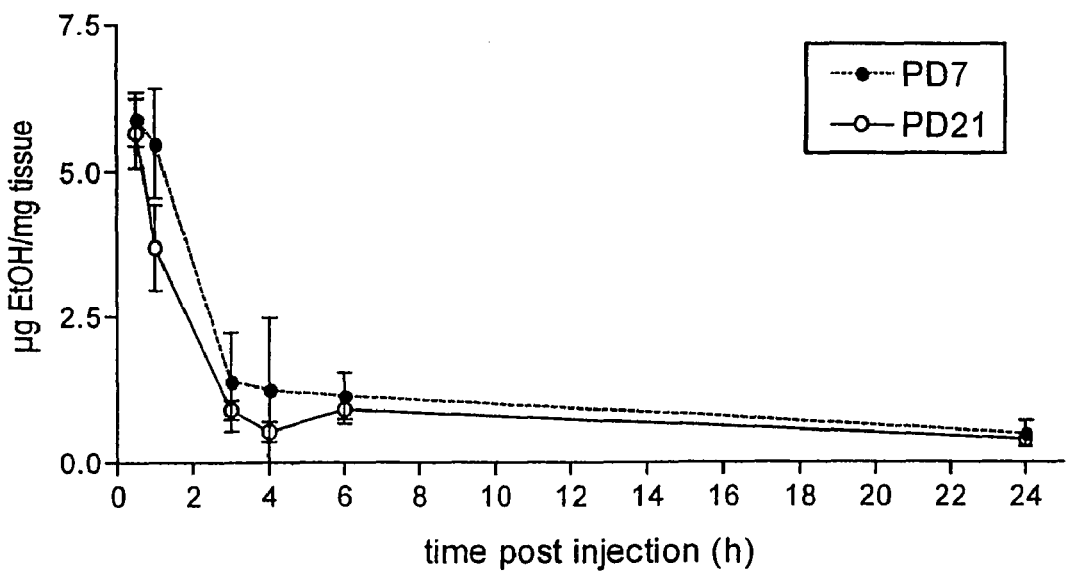
FIGS. 14A-14B are plots of the ethanol level in blood (μg ethanol/mL blood.
Figure 14B:
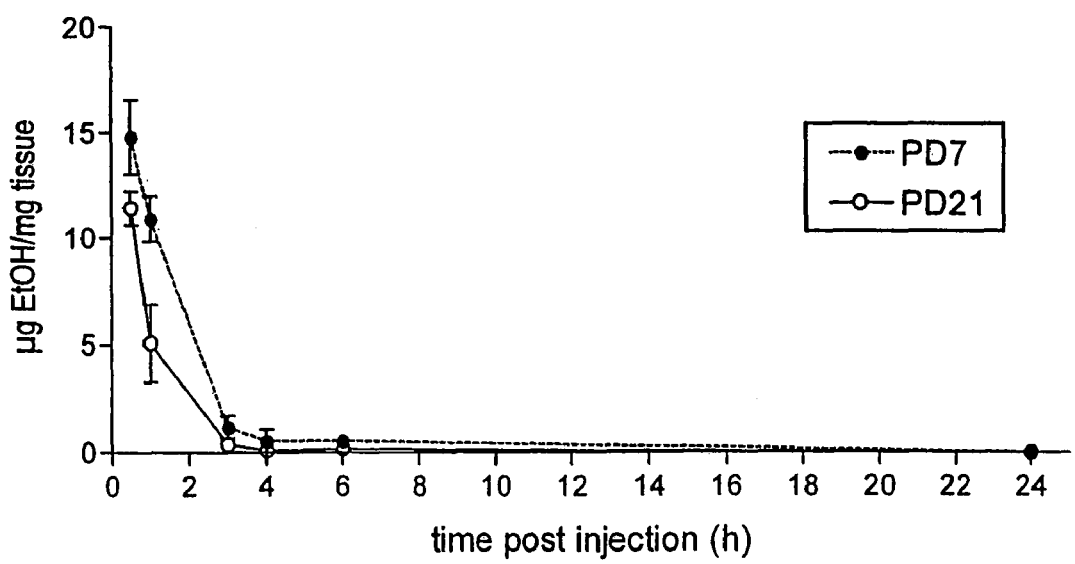

FIG. 14A shows the ethanol level in blood for 7 day old (closed circles) and 21 day old rats (open circles) as a function of time post ethanol injection. FIG. 14B is a similar plot for the ethanol concentration in the spinal cord (reported as μg ethanol/mg tissue). For both 7 day old and 21 day old rats, blood EtOH concentrations reached similar peak levels at 30 minutes post-ethanol injection. At this timepoint, maximal blood EtOH concentrations were 5.91±0.46 μg/mL for 7 day old pups and 5.67±0.60 μg/mL for 21 day old rats (FIG. 14A).

The elimination pharmacokinetics are summarized in Table 1. Elimination of EtOH from blood exhibited an initial fast rate (early phase) followed by a slower rate (late phase). Both age groups exhibited dramatically decreased levels of EtOH by 3 hours post-ethanol injection with similar early phase half lives, 1.9 and 1.7 h, respectively. 21 day old rats exhibited a late phase half-life that extended 4 hours beyond that of the 7 day old rats and at 24 hours post-injection, a low concentration of EtOH was still detectable.

TABLE 1

| Region | Rat Age | T ½ Early (hours) | T ½ Late (hours) |
|---|---|---|---|
| Blood | 7 day old | 1.9 | 18.1 |
|  | 21 day old | 1.7 | 22.5 |

TABLE 1-continued

| Region | Rat Age | T ½ Early (hours) | T ½ Late (hours) |
|---|---|---|---|
| Spinal Cord | 7 day old | 1.6 | 11.5 |
| | 21 day old | 1.5 | 11.7 |

Nociceptive afferent fibers terminate on neurons in the dorsal horn of the spinal cord, thus the concentration and kinetics of EtOH in spinal cord tissue was also examined. As shown in FIG. 14B and in Table 1, in contrast to blood, there were pronounced differences in EtOH concentrations between 7 day old and 21 day old rats in spinal cord EtOH concentration. Peak EtOH levels occurred at 30 minutes post injection and decreased to minimal levels by 3 hours post-injection with similar early phase half lives; 1.6 h for P7 rats and 1.5 h for P21 rats (FIG. 14B, Table 1). The maximal EtOH concentration for 7 day old rats, 14.8 µg/mg tissue, was higher than that for 21 day old rats, 11.4 µg/mg tissue, and remained higher throughout the early phase. Spinal cord EtOH decreased to nearly undetectable-levels at a faster rate than blood EtOH levels as evidenced by a later-phase half-life that was 50% that of the half life for blood EtOH levels.

In order to investigate the roles of PKCε and PKCγ in mediating ethanol withdrawal-induced pain, 7 day old and 21 day old rats were intrathecally administered PKCε peptide inhibitor (εV1-2; SEQ ID NO:1) or PKCγ peptide inhibitor (γV5-3; SEQ ID NO:2) 1 hour prior to the predicted onset of withdrawal hyperalgesia. Control rats were injected with vehicle containing the Tat carrier protein (SEQ ID NO:3) to which the inhibitors were conjugated.

Figure 15A:
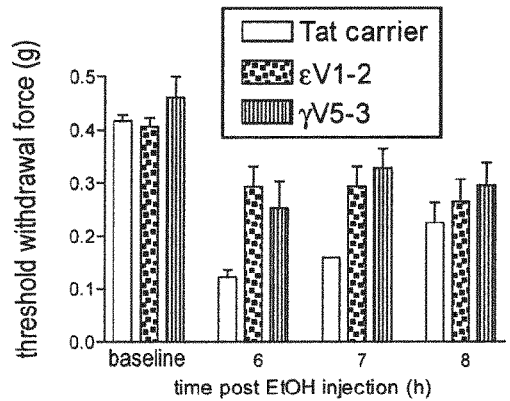
FIGS. 15A-15D are bar graphs showing the threshold withdrawal force, in grams, at various times post-ethanol injection (FIGS. 15A, 15C) or post-saline injection (control, FIGS. 15B, 15D) for 7 day old rat pups (FIGS. 15A, 15B) treated with εV1-2 (dotted bars), γV5-3 (vertical striped bars), or Tat alone (open bars) and for 21 day old rat pups (FIGS. 15C, 15D) similarly treated.
Figure 15B:
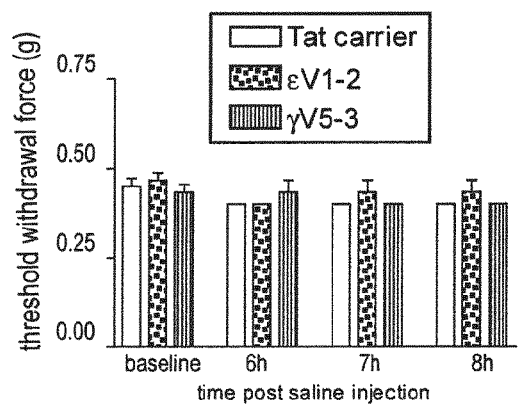
Figure 15C:
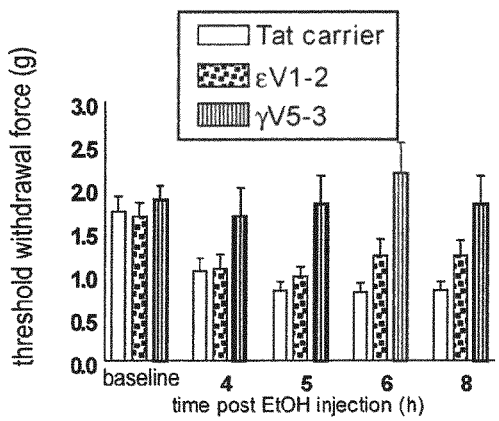
Figure 15D:
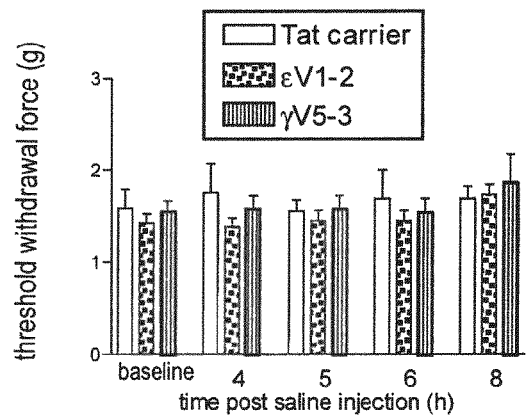

Results of mechanical allodynia testing are shown in FIGS. 15A-15D. FIGS. 15A-15B are bar graphs showing the threshold withdrawal force for various times post-ethanol injection (FIG. 15A) or post-saline injection (control, FIG. 15B) for 7 day old rat rats treated with εV1-2 (dotted bars), γV5-3 (vertical striped bars), or Tat alone (open bars). FIGS. 15C-15D are similar bar graphs for 21 day old rat rats. With respect to the 7 day old rats, administration of εPKC (dotted bars) and γPKC (vertical striped bars) peptide inhibitors attenuated mechanical allodynia at both the 6 hour and 7 hour post-EtOH injection time points, as compared to Tat carrier-treated rats (open bars, FIG. 15A). At 8 hours, all rats exhibited similar threshold withdrawal responses, which were significantly lower than pre-EtOH baseline levels regardless of treatment group. The PKC isozyme-specific inhibitors had no effect on threshold paw withdrawals in the absence of EtOH (FIG. 15B).

With respect to the 21 day rats, FIG. 15C shows that the PKCε inhibitor (dotted bars) slightly attenuated the response at 6 hours and 8 hours post ethanol injection. The PKCγ inhibitor (vertical striped bars) prevented a decrease in threshold withdrawal response, and effectively maintained the withdrawal responses equal to pre-EtOH baseline levels (FIG. 15C, baseline) and to levels in which rats received saline (FIG. 15D) rather than EtOH.

Figure 16A:
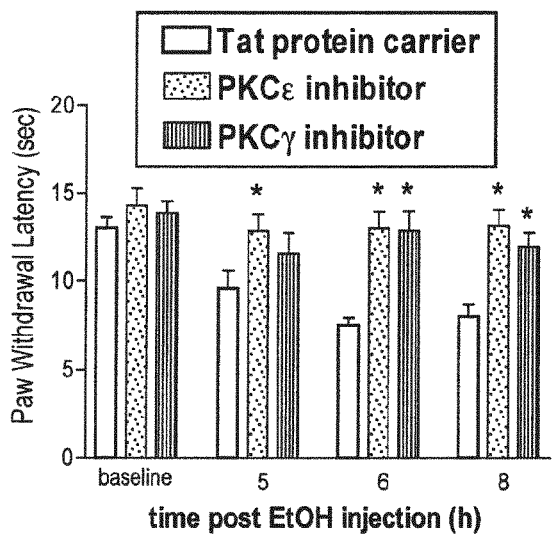
FIGS. 16A-16B are bar graphs showing the paw withdrawal latency, in seconds, for 7 day old rat pups as a function of time post-ethanol (FIG. 16A) or post-saline (FIG. 16B)
Figure 16B:
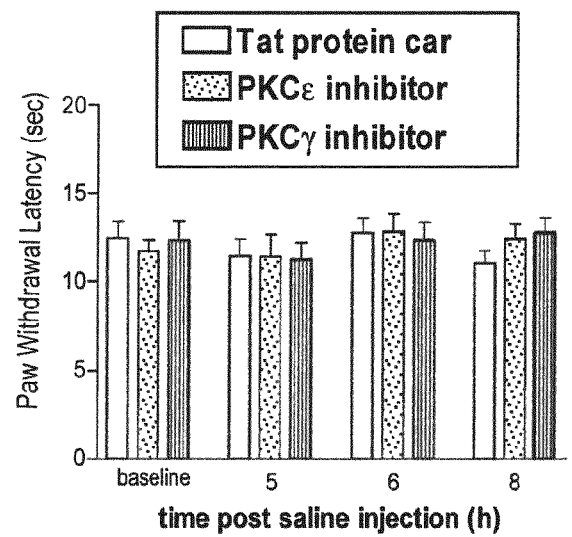

FIGS. 16A-16B show the results for the thermal hyperalgesia evaluation. FIG. 16A is a bar graph showing the paw withdrawal latency, in seconds, for 7 day old rat pups prior to ethanol injection (baseline) and at 5 hours, 6 hours, and 8 hours post ethanol injection. At 4 hours post-ethanol injection, a PKC inhibitor peptide, εPKC V1-2 (SEQ ID NO:1; dotted bars) or γPKC V5-3 (SEQ ID NO:2, vertical striped bars), or Tat carrier peptide alone (SEQ ID NO:3, open bars) was administered intrathecally (Example 4). FIG. 16B is a similar graph for animals treated with saline, rather than ethanol.

FIG. 16A shows that administration of both εPKC and γPKC peptide inhibitors completely prevented thermal hyperalgesia in 7 day old rat rats. Rats that had received PKC-isozyme-specific inhibitors had paw withdrawal latencies similar to those of saline-treated animals (FIG. 16B).

To determine if EtOH alters the expression and cellular localization of εPKC and γPKC, immunohistochemistry was performed on L4/5 dorsal root ganglion (DRG) and L4/5 lumbar spinal cord sections, as described in Example 4. Rat at postnatal days 7 and 21, treated with saline or 4 g/kg 15% EtOH, were euthanized at 2, 4, or 6 hours post injection for isolation of the lumbar spinal cords. In 7 day old rats injected with saline, a small percentage of cells stained positive for εPKC (data not shown). After a 2 hour exposure to EtOH, the percentage of cells staining positive for εPKC increased, as did staining density in individual cells (data not shown). By 4 and 6 hours, the number of cells staining positive for εPKC returned to levels equivalent to saline injected animals. In 21 day old rats injected with saline, more cells staining positive for εPKC, relative to the saline-treated 7 day old pups, were observed. Treatment with EtOH did not result in an increase in the number of positive staining cells or in the staining intensity within positively stained cells (data not shown). εPKC staining appeared to be predominantly cytoplasmic.

In 7 day old rats, few γPKC positive neuronal somata are observed in lamina II of the lumbar spinal cord in control animals. γPKC staining in EtOH-injected animals did not differ from saline injected animals at 2 hours and 4 hours post injection, but the number of somata staining positive for γPKC increased 4-fold above saline control levels by 6 hours post injection (data not shown). In 21 day old rats, there was abundant γPKC staining in the cell somata. While the number of γPKC positive somata did not change following EtOH, γPKC staining intensity increased by 2 hours post-EtOH injection and remained elevated at 6 hours post injection (data not shown). In addition to increased staining intensity, magnification of tissues demonstrated that γPKC in saline-treated pups was predominantly cytoplasmic; by 2 hours post-EtOH injection, γPKC had translocated to the plasma membrane; by 6 hours, γPKC was once again predominantly cytoplasmic (data not shown).

III. Utility

Accordingly, administration of a peptide or other compound that antagonizes the activity of εPKC or of γPKC is contemplated for managing withdrawal from a habit-forming or addictive drug. In the studies described above, exemplary peptides specific for the ε and γ isozymes of PKC were shown to prevent or attenuate symptoms associated withdrawal from an addictive drug.

It will be appreciated that the peptides identified herein as SEQ ID NO:1 and SEQ ID NO:2 are merely exemplary, and modifications, fragments and derivatives, as well as other peptides derived from the εPKC sequence that have an activity similar to that demonstrated herein, are contemplated. Suitable modifications, such as conservative amino acid substitutions, are readily determined by those of skill in the art. Exemplary modifications for SEQ ID NO:2 (RLVLAS) include the following changes shown in lower case: kLVLAS (SEQ ID NO:4); RLVLgS (SEQ ID NO:5); RLVLpS (SEQ ID NO:6); RLVLnS (SEQ ID NO:7), and any combination of the above. Other modifications include changes of one or two L to I or V, such as RiVLAS (SEQ ID NO:8); RLViAS (SEQ ID NO:9); or RiViAS (SEQ ID NO:10). Also, L and V can be changed to V, L, I, R, and/or D, as in RLiLAS (SEQ ID NO:11), RLdLAS (SEQ ID NO:12), and RidLAS (SEQ ID NO:13) or RridAS (SEQ ID NO:14). Any modification that retain the desired activity are suitable. Thus, in all of the exemplary fragments recited above, conservative modifications and other modifications that do not appreciably alter the activity can be made and fall within the contemplated peptides.

It will be appreciated that the peptides can be used in native form or modified by conjugation to a carrier. In native form, the peptide can be formulated as needed to facilitate its transport into a cell. Suitable formulations for cell permeation are known in the art and include, for example, micelles, liposomes (charged and uncharged), and lipophilic media. When linked to a carrier, one of skill can select from a variety of peptide carriers known in the art. In addition to the Tat carrier used in the studies described above, carriers based on *Drosophila* Antennapedia homeodomain (SEQ ID NO:15; Théodore, L., et al. *J. Neurosci.* 15:7158 (1995); Johnson, J. A., et al., *Circ. Res.* 79:1086 (1996b)), where the PKC peptide is cross-linked via an N-terminal Cys-Cys bond to the Antennapedia carrier, are suitable. Polyarginine is another exemplary carrier peptide (Mitchell et al., *J. Peptide Res.*, 56:318-325 (2000); Rolhbard et al., *Nature Med.*, 6:1253-1257 (2000)).

All peptides described herein can be prepared by chemical synthesis using either automated or manual solid phase synthetic technologies, known in the art. The peptides can also be prepared recombinantly, using techniques known in the art.

The peptides are prepared for administration by combining with a pharmaceutically-acceptable carrier or diluent. Thus, a further aspect of the invention provides pharmaceutical compositions comprising a γPKC peptide or an εPKC peptide in a dosage form suitable for administration to a subject in need of pain management. Exemplary dosage forms include, but are not limited to, the peptides formulated in pharmaceutical carriers such as starch, lactose, talc, magnesium stearate, aqueous solutions, oil-water emulsions, and the like. Dosage forms suitable for injection by any route, including but not limited to intrathecal, intravenous, intraperitoneal, intramuscular, subcutaneous, can be prepared using pharmaceutical carriers such as buffered-aqueous or non-aqueous media. The peptides can be locally administered near a site of inflammation or peripheral nerve damage, by, for example, topical application, dermal or transdermal administration, or intradermal injection. Mucosal delivery is also contemplated, where the peptides are formulated for sublingual, vaginal, intranasal, or ocular delivery. It will be appreciated that certain forms of administration can achieve an initial localized site of delivery that becomes more widespread over time. For example, a buccal patch or a vaginal suppository provides an initially localized delivery at the site of application. Over time, the peptides travel in the body fluids (lymph, blood) from the site of delivery to provide a more widespread area of action. The extent of delivery can be controlled via selection of formulation and route of administration, as known to those of skill in the pharmaceutical formulation arts.

The amount of the peptide in the composition can be varied so that a suitable dose is obtained and an effective analgesic effect is achieved. The dosage will depend on a number of factors such as the route of administration, the duration of treatment, the size and physical condition of the patient, the potency of the peptide and the patient's response. Effective amounts of the peptide can be estimated by testing the peptide in one or more the pain models described herein.

The peptides can be administered as needed, hourly, several times per day, daily, or as often as the person experiencing the pain or that person's physician deems appropriate. The peptides can be administered prophylactically, in anticipation of pain, or can be administered as needed prior to or during an acute episode of pain. The peptides can be administered on an on-going basis for management of chronic pain, or can be administered on a short term basis prior to after an episode of pain, for example, prior to and/or after surgery.

The invention further contemplates a kit comprising components for a user to employ in managing the symptoms of withdrawal from an addictive agent. The user may be a health care provider, such as a nurse or a doctor, caring for a patient being treated with an addictive agent or being treated for abuse of an addictive agent. The user can also be the person taking an addictive agent whether or not clinical addiction has occurred.

The kits includes (i) at least one container containing a peptide having isozyme-specific inhibitory activity for γPKC and/or εPCK; and (ii) instructions for use. In one embodiment, the kit is comprised of a first container containing a peptide having isozyme-specific inhibitory activity for εPKC, such as the peptide identified herein by SEQ ID NO:1 or any of the modifications discussed above.

The kit can also include a second container containing a peptide having isozyme-specific inhibitory activity for γPKC, such as the peptide identified herein by SEQ ID NO:2 or any of the modifications discussed above. Kits containing two vials, one containing an ε-specific PKC peptide, the other containing a γ-specific isozyme peptide, will include instructions to direct a user to administer the peptide having isozyme-specific inhibitory activity for εPKC prior to or concurrent with administration of an addictive agent. The user is further instructed to administer the peptide having isozyme-specific inhibitory activity for γPKC after administration of an addictive agent.

The peptides in the kit can be provided ready for use or in a form requiring addition of a sterile fluid, such as saline. Naturally, if a sterile fluid is required, the kit could include a quantity of the necessary fluid and a syringe, if needed for injection. Peptides formulated ready for use intends dosage forms for single or multiple use in any of the forms discussed above for any route of administration.

The invention also contemplates a therapeutic regimen for managing withdrawal symptoms in neonates. The studies described here employed postnatal day 7 rats, which correspond developmentally to newborn human infants, and postnatal day 21 rats, which developmentally correspond to a human preschool age child (Fitzgerald and Anand, Pain Management in Infants, Children and Adolescents (Schetchter et al., Eds.), pp 11-32. Baltimore, Md., Williams and Williams, 1993). Human infants are routinely treated with opiods for pain relief and for sedation during mechanical ventilation. Many of these infants demonstrate symptoms of neonatal abstinance syndrome, a developmentally specific equivalent of opiate withdrawal (Norton, S., *Neonatal Netw.*, 7:25-28 (1988)). From the data described herein on postnatal day 7 rats, morphine exposure produced an early phase of primary afferent sensitization dependent upon translocation of εPKC, followed by a later phase involving spinal sensitization mediated by γPKC-containing neurons within the spinal cord. This data suggests a temporal therapy for treatment of opiate tolerance and withdrawal in the human neonatal population, by administering a peptide having εPKC specific activity during the early phase of sensitization, and, if desired, a peptide having γPKC specific activity during later phases of sensitization.

From the foregoing, it can be seen how various objects and features of the invention are met. Methods for attenuating withdrawal symptoms associated with cessation of use of an addictive agent are provided. Most generally, the method includes administering to a subject, typically a mammal (especially human), a peptide having isozyme specific activity for εPKC or for γPKC. In one embodiment of the method, both peptides are administered in a temporal fashion, where the peptide having specific activity for εPKC isozyme is administered prior to or concurrent with administration of the addictive agent. A peptide having specific activity for the γPKC isozyme is administered after the addictive agent is given to the subject. "After" intends administration of the γPKC isozyme specific peptide immediately administration of the addictive agent or minutes or hours after administration of the addictive agent.

IV. Examples

The following example further illustrates the invention described herein and is in no way intended to limit the scope of the invention.

Materials and Methods

All peptides were synthesized at Stanford's Protein and Nuclei Acid facility and conjugated to Tat, amino acids 47-57 (SEQ ID NO:3) via a cysteine-cysteine bond at their N termini. The εPKC antagonist, εV1-2 (SEQ ID NO:1) and the γPKC antagonist, γV5-3 (SEQ ID NO:2) were used at >90% purity.

Example 1

In Vitro Measurement of sVRP

Spinal cords from 4-7 day old rats (Charles River Laboratories) were removed and arranged for electrophysiological recording of the slow ventral root potentials (sVRP) (Woodley S. J., et al., *Brain Res.*, 559:17-21 (1991). Briefly, pups were decapitated under halothane anesthesia and the spinal cord removed to an oxygenated artificial cerebrospinal fluid solution. A suction stimulating electrode was placed on a lumbar dorsal root and a suction recording electrode on the corresponding ipsilateral ventral root. Square wave stimuli 0.2 ms in duration were administered at a constant frequency of 1/30 seconds throughout the experiment. Test agents were applied and the responses were recorded, digitized, and area under the curve measured.

After a baseline reading of the sVRP, morphine (200 nM) was applied to the isolated spinal cords. The sVRP was again recorded to characterize the response to morphine. Naloxone (200 nM) was then applied and the sVRPs recorded. The results are shown in FIGS. 1A-1D.

FIGS. 2A-2D show the results after application of non-specific PKC antagonist, GF109203X (1.2 µM), and of an inhibitor specific to Ca++-dependent PKC isoforms, Go6976 (1 µM).

FIGS. 3A-3B show the results after application of the εPCK antagonist (εV1-2; SEQ ID NO:1, 2 nM), conjugated to a peptide carrier (Tat; SEQ ID NO:3) and the Tat peptide alone (2 nM; SEQ ID NO:3). FIGS. 3C-3D show the results after application of γPKC (γV5-3; SEQ ID NO:2, 4 nM) conjugated to a peptide carrier (Tat; SEQ ID NO:3) and of the Tat peptide alone (4 nm; SEQ ID NO:3).

Example 2

In Vivo Mechanical Threshold and Thermal Paw Withdrawal Studies

Postnatal day 7 Sprague-Dawley rats (Charles River Laboratories) of both sexes were used. For all behavioural experiments rats were maintained at nesting temperature with overhead heatlamps.

To measure mechanical thresholds, rats were placed on an elevated wire mesh (2 mm openings). Von Frey hairs (Stoelting Co., WoodDale, Ill., USA) were used to elicit a cutaneous flexion withdrawal response as described by Fitzgerald et al. (Fitzgerald M., et al., PAIN MANAGEMENT IN INFANTS, CHILDREN AND ADOLESCENTS; Schetchter and Yaster, Eds., pp 11-32, Williams and Williams (Baltimore, Md.) (1993). Von Frey hairs of increasing intensity were applied three times to the plantar surface of the left hind paw until a paw withdrawal was elicited. The lowest intensity Von Frey hair required to produce a withdrawal reflex was recorded as the response threshold to a low-intensity mechanical stimulus.

Thermal paw withdrawal latencies were measured using the Ugo Basile Plantar Testing apparatus (Stoelting Co., WoodDale, Ill., USA). Briefly, postnatal day 7 rats were placed under inverted Plexiglas enclosures and the plantar surface of the left hindpaw was heated from below with the IR intensity of the lamp set at 30. Two baseline thermal response latency measures were collected prior to morphine administration with a cut-off of 20 seconds enlisted to prevent tissue damage.

Postnatal day 7 rats were administered 1 mg/kg morphine sulfate (Sigma) subcutaneously in 50 µl saline. Mechanical thresholds were measured 15 minutes later to establish analgesia. Rats were returned to their dam. At 30 or 120 minutes post morphine, rats were administered 0.25 mg/kg naloxone (Sigma) subcutaneously in 50 µl saline. Mechanical thresholds and thermal paw withdrawal latencies were measured in 10 minute intervals. Tat conjugated peptide inhibitors specific to the ε (εV1-2; SEQ ID NO:1, 10 µM) and γ (γV3-5; SEQ ID NO:2, 10 µM) isoforms of PKC, Tat carrier (10 µM), or saline were administered in 5 µl volumes intrathecally via direct lumbar puncture using a sterile 29 gauge 3/10 cc insulin syringe in rats lightly anesthetized with halothane. To allow for complete recovery from anesthetic, animals were administered peptides or control solutions 30 minutes prior to naloxone. The results are shown in FIGS. 4A-4B and 5B-5C.

For natural withdrawal studies, rats were administered morphine (1 mg/kg) followed 2.5 hours later by εV1-2 (10 µM), γV3-5 (10 µM), Tat carrier (10 µM), or saline. Mechanical thresholds and thermal paw withdrawal latencies were examined at 3, 4, 5, and 6 hours post-morphine. The results are shown in FIGS. 6B-6C.

An unpaired T-test was used to determine the significance of post-naloxone measures from baseline measures. Significance between treatment groups for PKC inhibitor studies both in vivo and in vitro was determined by one way analysis of variance (ANOVA) followed by a post-hoc Bonferroni analysis. P-values<0.05 were considered significant. All statistical analysis was done with GraphPad Prism version 3.02.

Example 3

Effect of γPKC Peptides on Alcohol Withdrawal Hyperresponsiveness In Vitro

Sprague-Dawley rats at postnatal day 7-10 were anesthetized with halothane, decapitated, and the spinal cords were quickly removed. Slices 350 mm thick were sectioned from the lumbar region. Whole cell voltage clamp recordings were made from visually-identified motor neurons using infrared video microscopy, a 60× water immersion lens, and a Multi-Clamp 700A patch clamp amplifier. Cells were held at a holding potential of −60 mV in artificial cerebrospinal fluid (ACSF) containing bicuculline methiodide (10 mM), strychnine (5 mM), and tetrodotoxin (0.5 mM). Postsynaptic currents were evoked by direct pressure application of 2 mM N-methyl-D-aspartate (NMDA) from a pipette positioned near the recorded cell at 1-2 min intervals, as illustrated in FIG. 7A. The area of evoked currents during and following 100 mM ethanol (EtOH) application was measured and normalized to the average baseline current area during the 10 minutes preceding EtOH application. Data are expressed as mean+/−SEM. Statistical significance was determined by one-way ANOVA followed by Dunn's or Tukey's multiple comparison test with significance set at $p<0.05$.

Fluorescence immunocytochemical studies were performed on spinal cord sections (30 mm) from control slices (perfused with ACSF for 70 minutes) and EtOH treated slices (perfused with ACSF for 30 minutes followed by 20 min 100 mM EtOH and 20 min wash with ACSF). The sections were incubated with a rabbit anti-PKCg polyclonal antibody (1:500) overnight at 4° C. In some cord sections, a mouse anti-neuronal nuclei monoclonal antibody (NeuN, 1:750) was added to identify neurons. After several washes with ACSF, the sections were labeled for 2 hours at room temperature with fluorescein-labeled secondary antibodies (1:500). Double immunofluorescence was assessed with a laser confocal microscope.

Results are shown in FIGS. 7-11.

Example 4

Effect of γPKC and εPKC Peptides on Alcohol Withdrawal-Induced Allodynia and Hyperalgesia In Vivo 1. Animals Sprague-Dawley rats (Charles River, Mass.) were housed with dams and were exposed to a 12/12 light/dark cycle with free access to food and water. Unless otherwise stated, experiments were performed on 7-day old male and female pups (14-17 g) or on 21-day old male animals (45-55 g). 7 day-old pups were maintained at nest temperature by overhead heat lamps for both mechanical and thermal testing.

7 day-old rat pups were intraperitoneally (i.p.) injected with a single dose of 1 g/kg or 4 g/kg 15% EtOH or with saline. 21 day-old rat pups were i.p. injected with 0.5 g/kg or 4 g/kg 15% EtOH or with saline.

2. Allodynia and Hyperalgesia Testing

Mechanical allodynia testing was performed as follows. Each rat, under non-restrained conditions, was placed singly in a Plexiglass cage upon an elevated aluminum screen surface with 1 mm mesh openings. 21-day old animals were previously acclimated to this environment and to the experimenter. 7 day-old and 21-day old pups were subjected to three tactile stimulations on the hind paw with 0.04 g to 1.4 g or with 0.16 to 6 g von Frey filaments, respectively (Stoelting Co., Wood Dale, Ill.). The threshold value for pain was defined as the lifting of the paw upon all three stimulations as previously described (Fitzgerald M., et al., PAIN MANAGEMENT IN INFANTS, CHILDREN AND ADOLESCENTS; Schetchter and Yaster, Eds., pp 11-32, Williams and Williams (Baltimore, Md.) (1993). Baseline testing in 7 day-old pups was conducted prior to EtOH treatment and was subsequently measured every hour up to 6 hours, and at 8, 10, 12, and 24 hours post injection. Baseline testing in 21 day-old pups was conducted as above and at every 2 hours up to 8 hours post injection, and at 24, 48, and 72 hours post ethanol injection. Allodynia was defined as a threshold force below the threshold force required to elicit a response in saline controls.

Thermal hyperalgesia testing was performed as follows. Thermal paw withdrawal latencies were measured using the Ugo Basile Plantar Testing apparatus (Stoelting Co., Wood-Dale, Ill., USA). Briefly, postnatal day 7 or 21 rats were placed under inverted Plexiglas enclosures and the plantar surface of the hindpaw was heated from below with the IR intensity of the lamp set at 30 or 40, respectively. Three baseline thermal response latency measures were collected prior to EtOH administration with a cut-off of 20 seconds enlisted to prevent tissue damage. Following EtOH administration, 2 readings separated by 10 minutes were taken every 2 hours up to 8 hours and then again at 24 hours for each pup. Reported paw withdrawal latencies represent the mean of individual measurements.

Results are shown in FIGS. 12A-12B and FIGS. 13A-13B.

To determine the involvement of εPKC and γPKC in withdrawal-induced mechanical allodynia and thermal hyperalgesia, 7 day old and 21 day old rats were administered inhibitor peptides 5 hours (7 day old pups) or 4 hours (21 day old pups) following a single dose of 4 g/kg 15% EtOH or saline (i.p.). For thermal testing, 7 day old pups received inhibitor peptides at 4 hours post-EtOH administration. Intrathecal peptide drug delivery was via direct lumbar puncture under halothane anesthesia with 5 μL (7 day old pups) or 10 μL (21 day old pups) of 20 μM PKCε (εV1-2; SEQ ID NO:1) or PKCγ (γV5-3; SEQ ID NO:2) inhibitor peptide linked to a Tat protein carrier (SEQ ID NO:3). PKC isozyme-specific inhibitors were administered 1 hour prior to the previously determined time for onset of hyperalgesia/allodynia. Mechanical allodynia and thermal hyperalgesia testing were performed as stated above with the experimenter blinded to peptide drug treatment. Results are shown in FIGS. 15A-15D and 16A-16B.

3. Determination of Blood and Spinal Cord Ethanol Levels 7 day old and 21 day old rat pups were administered 4 g/kg of 15% EtOH (i.p.) according to the acute procedure described above. Animals were deeply anesthetized at various times following injection and blood was collected into heparin-containing syringes via direct cardiac puncture. Spinal cord and blood were removed and stored in microfuge tubes at −80° C. until analysis. At the time of analysis, tissue was homogenized in 1 μL 6.25% (w/v) trichloroacetic acid (TCA)/mg of tissue using a Polytron® tissue homogenizer for 5 seconds. An aliquot of whole blood (100 μL) was added to 900 μL TCA and vortexed. Tissue and blood samples were centrifuged at 10,000 rpm for 5 minutes at room temperature and EtOH content was determined using a colorimetric assay (Sigma Diagnostics, St. Louis) adapted for a 96-well format according to manufacturer's instructions. Results are shown in FIGS. 14A-14B.

4. Immunohistochemistry

Animals administered a single dose of 4 g/kg 15% EtOH or saline (i.p.) were deeply anesthetized with halothane and euthanized at 2, 4, or 6 hours post injection by transcardiac perfusion (phosphate-buffered saline wash, followed by 4% formaldehyde in PBS, pH 7.4). Following perfusion, lumbar spinal cord and L4/L5 dorsal root ganglia (DRG) were isolated and post-fixed for 3 hours in 4% formaldehyde solution followed by cryoprotection in 30% sucrose/PBS at 4° C. Sections were freeze-mounted in OCT-embedding medium on cork blocks and stored at −80° C. until analysis. For spinal cord sections, free-floating immunohistochemistry was performed on 30 μm L4-L5 spinal sections. Dorsal root ganglia were cut on a cryostat at 10 μm and slide mounted. Slides were heated overnight at 32° C. Immunohistochemistry was performed utilizing an avidin-biotin complex (ABC) technique as previously described (Sweitzer et al., *Brain Res.*, 829(1-2):209-221 (1999)). Rabbit polyclonal antibodies to γPKC (1:500 from Santa Cruz) or εPKC (1:1,000 from Santa Cruz) were used. Immunohistochemistry was scored blinded to experimental conditions.

For both spinal cord tissues and DRG, densitometry using ImageJ software was performed on at least three sections from each of three individual animals.

5. Statistics

Significant differences between treatment groups and saline controls were demonstrated by one-way analysis of variance. The medians of groups were compared by the post-hoc test of Newman-Keuls. Significant differences between treatment groups and baseline were determined using a non-parametric t-test. All statistics were performed using Graph-Pad Prizm, version 3.0 (GraphPad Software, San Diego, Calif.).

Although the invention has been described with respect to particular embodiments, it will be apparent to those skilled in the art that various changes and modifications can be made without departing from the invention.

---

It is claimed:

1. A kit comprising,
   i) at least one container containing a peptide having isozyme-specific inhibitory activity for γPKC, wherein said peptide consists of a sequence selected from the group consisting of SEQ ID NO:2 and SEQ ID NOs:4-14; and
   (ii) instructions for use.

2. The kit according to claim 1, wherein said instructions for use direct a user to administer said peptide having isozyme-specific inhibitory activity for γPKC after administration of an addictive agent.

3. The kit according to claim 1, wherein said peptide is formulated for intracellular delivery by conjugation to a carrier peptide.

4. The kit according to claim 3, wherein said peptide is conjugated at its N-terminus to a carrier selected from the group consisting of peptides identified as SEQ ID NO:3 and polyarginine.

5. A kit comprising,
   i) at least one container containing a peptide having isozyme-specific inhibitory activity for γPKC; and
   (ii) instructions for use;
   wherein said peptide is formulated for intracellular delivery by conjugation to a carrier peptide.

6. The kit according to claim 5, wherein said peptide is conjugated at its N-terminus to a carrier selected from the group consisting of peptides identified as SEQ ID NO:3 and polyarginine.

* * * * *

SEQUENCE LISTING

```
<160> NUMBER OF SEQ ID NOS: 15

<210> SEQ ID NO 1
<211> LENGTH: 8
<212> TYPE: PRT
<213> ORGANISM: Homo sapiens

<400> SEQUENCE: 1

Glu Ala Val Ser Leu Lys Pro Thr
 1               5

<210> SEQ ID NO 2
<211> LENGTH: 6
<212> TYPE: PRT
<213> ORGANISM: Homo sapiens

<400> SEQUENCE: 2

Arg Leu Val Leu Ala Ser
 1               5

<210> SEQ ID NO 3
<211> LENGTH: 11
<212> TYPE: PRT
<213> ORGANISM: Human immunodeficiency virus 1

<400> SEQUENCE: 3

Tyr Gly Arg Lys Lys Arg Arg Gln Arg Arg Arg
 1               5                  10

<210> SEQ ID NO 4
<211> LENGTH: 6
<212> TYPE: PRT
<213> ORGANISM: Artificial
<220> FEATURE:
<223> OTHER INFORMATION: synthetic modified inhibitor of the gamma
      isozyme of PKC

<400> SEQUENCE: 4

Lys Leu Val Leu Ala Ser
 1               5

<210> SEQ ID NO 5
<211> LENGTH: 6
```

```
<212> TYPE: PRT
<213> ORGANISM: Artificial
<220> FEATURE:
<223> OTHER INFORMATION: synthetic modified inhibitor of the gamma
      isozyme of PKC

<400> SEQUENCE: 5

Arg Leu Val Leu Gly Ser
 1               5

<210> SEQ ID NO 6
<211> LENGTH: 6
<212> TYPE: PRT
<213> ORGANISM: Artificial
<220> FEATURE:
<223> OTHER INFORMATION: synthetic modified inhibitor of the gamma
      isozyme of PKC

<400> SEQUENCE: 6

Arg Leu Val Leu Pro Ser
 1               5

<210> SEQ ID NO 7
<211> LENGTH: 6
<212> TYPE: PRT
<213> ORGANISM: Artificial
<220> FEATURE:
<223> OTHER INFORMATION: synthetic modified inhibitor of the gamma
      isozyme of PKC

<400> SEQUENCE: 7

Arg Leu Val Leu Asn Ser
 1               5

<210> SEQ ID NO 8
<211> LENGTH: 6
<212> TYPE: PRT
<213> ORGANISM: Artificial
<220> FEATURE:
<223> OTHER INFORMATION: synthetic modified inhibitor of the gamma
      isozyme of PKC

<400> SEQUENCE: 8

Arg Ile Val Leu Ala Ser
 1               5

<210> SEQ ID NO 9
<211> LENGTH: 6
<212> TYPE: PRT
<213> ORGANISM: Artificial
<220> FEATURE:
<223> OTHER INFORMATION: synthetic modified inhibitor of the gamma
      isozyme of PKC

<400> SEQUENCE: 9

Arg Leu Val Ile Ala Ser
 1               5

<210> SEQ ID NO 10
<211> LENGTH: 6
<212> TYPE: PRT
<213> ORGANISM: Artificial Sequence
<220> FEATURE:
<223> OTHER INFORMATION: synthetic modified inhibitor of the gamma
      isozyme of PKC

<400> SEQUENCE: 10

Arg Ile Val Ile Ala Ser
```

-continued

```
<210> SEQ ID NO 11
<211> LENGTH: 6
<212> TYPE: PRT
<213> ORGANISM: Artificial Sequence
<220> FEATURE:
<223> OTHER INFORMATION: synthetic modified inhibitor of the gamma
      isozyme of PKC

<400> SEQUENCE: 11

Arg Leu Ile Leu Ala Ser
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic modified inhibitor of the gamma
      isozyme of PKC

<400> SEQUENCE: 12

Arg Leu Asp Leu Ala Ser
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic modified inhibitor of the gamma
      isozyme of PKC

<400> SEQUENCE: 13

Arg Ile Asp Leu Ala Ser
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic modified inhibitor of the gamma
      isozyme of PKC

<400> SEQUENCE: 14

Arg Arg Ile Asp Ala Ser
1               5

<210> SEQ ID NO 15
<211> LENGTH: 17
<212> TYPE: PRT
<213> ORGANISM: Artificial Sequence
<220> FEATURE:
<223> OTHER INFORMATION: synthetic modified Drosophila Antennapedia
      homeodomain-derived carrier peptide

<400> SEQUENCE: 15

Cys Arg Gln Ile Lys Ile Trp Phe Gln Asn Arg Met Lys Trp Lys
1               5                   10                  15

Lys
```